United States Patent [19]

Kaufman

[11] Patent Number: 5,543,118
[45] Date of Patent: * Aug. 6, 1996

[54] WASTE TREATMENT MATERIAL DISPENSING CANISTER

[76] Inventor: Jack W. Kaufman, 357 Frankel Blvd., Merrick, N.Y. 11566

[*] Notice: The term of this patent shall not extend beyond the expiration date of Pat. No. 5,391,351.

[21] Appl. No.: 306,363

[22] Filed: Sep. 15, 1994

Related U.S. Application Data

[63] Continuation-in-part of Ser. No. 507,966, Apr. 11, 1990, abandoned, which is a continuation-in-part of Ser. No. 215,370, Jul. 5, 1988, abandoned, which is a continuation-in-part of Ser. No. 105,875, Oct. 7, 1987, abandoned.

[51] Int. Cl.$^6$ .................. A61L 2/18; A61M 1/00
[52] U.S. Cl. .................. 422/292; 206/438; 604/321
[58] Field of Search .................. 604/319, 321; 215/212, 216; 220/323, 324, 356, 378; 206/438; 222/332, 336, 343; 422/83, 292

[56] References Cited

U.S. PATENT DOCUMENTS

| | | | |
|---|---|---|---|
| 3,221,918 | 12/1965 | Callegari | 220/323 |
| 3,990,604 | 11/1976 | Barnett et al. | 220/323 X |
| 4,346,711 | 8/1982 | Agdanowski et al. | 604/128 |
| 4,347,947 | 9/1982 | Hammes | 220/378 |
| 4,606,734 | 8/1986 | Larkin et al. | 604/84 |
| 4,610,374 | 9/1986 | Buehler | 222/83 |
| 4,620,598 | 11/1986 | Reeder | 222/83 X |
| 5,391,351 | 2/1995 | Kaufman | 422/28 |

Primary Examiner—Robert J. Warden
Assistant Examiner—E. Leigh Dawson
Attorney, Agent, or Firm—Lackenbach Siegel Marzullo Aronson & Greenspan

[57] ABSTRACT

A body waste fluids collecting container is used in the disposal of waste fluids drained from a body cavity of a patient. The collecting container has inlet and outlet ports, a collecting compartment for collecting body waste fluids drained from a patient, and a retaining compartment located within the collecting container. A composition for treating body waste fluids is located within the retaining compartment. At least one wall is located on the retaining compartment. The wall separates the composition from the collecting compartment. An actuator opens the wall and permits release of the composition from the retaining compartment upon actuation. A composition consists of a disinfectant, a xerogel, or combination thereof.

A waste treatment material dispensing device is also used with a closed waste fluid disposal vessel. The device contains waste treatment material and a container defining a storage volume for holding the waste treatment material. The container is capable of being lockably disposed in a port located on the waste fluid disposal vessel, and has an exit port open to the fluid disposal vessel. A wall covers the exit port and temporarily retains waste treatment material. An actuator is provided on the container for releasing the waste treatment material into a storage volume of the vessel.

8 Claims, 16 Drawing Sheets

FIG. 4
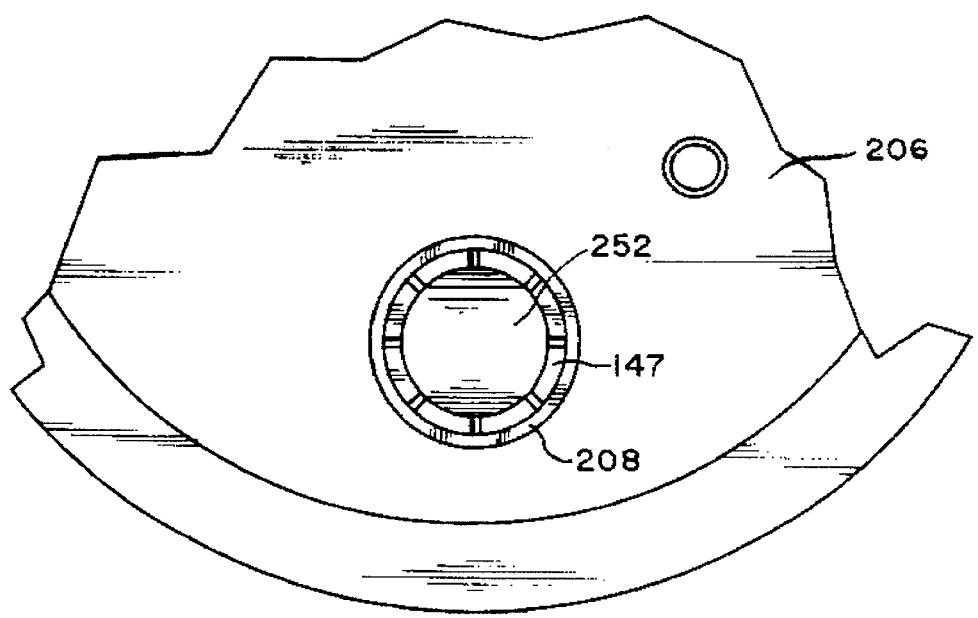
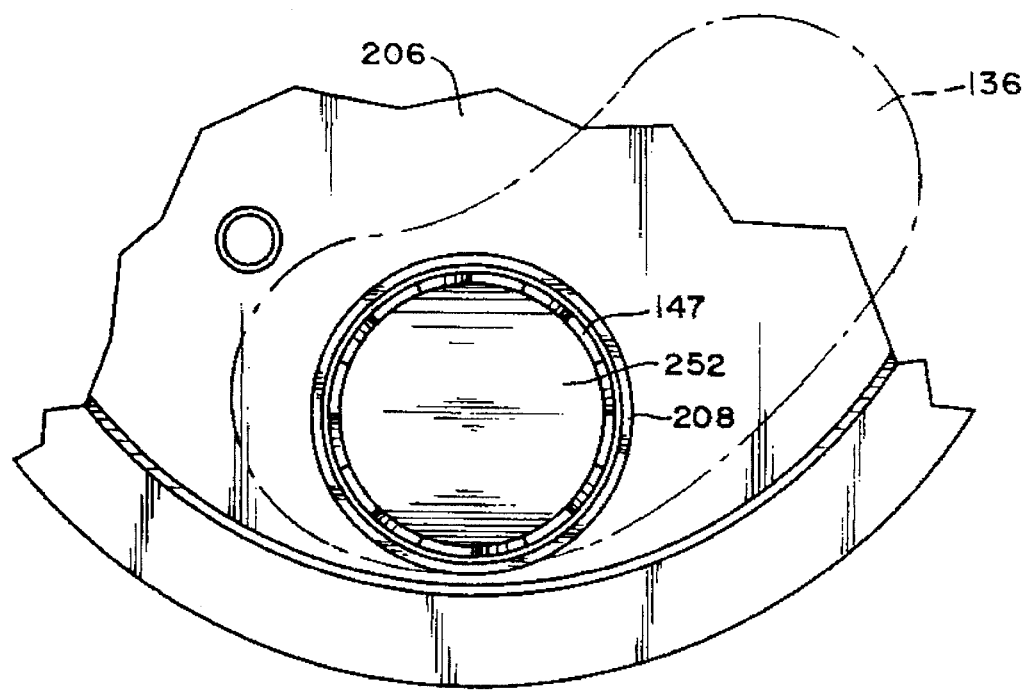
FIG. 5

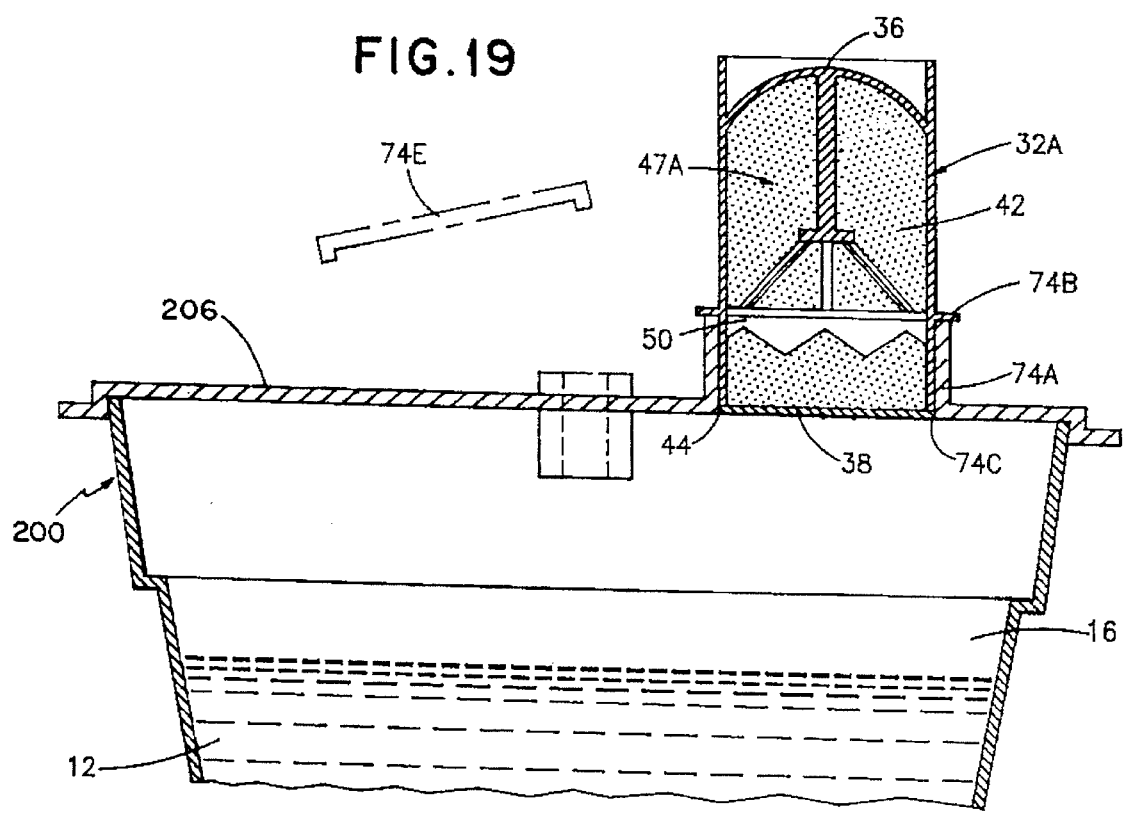
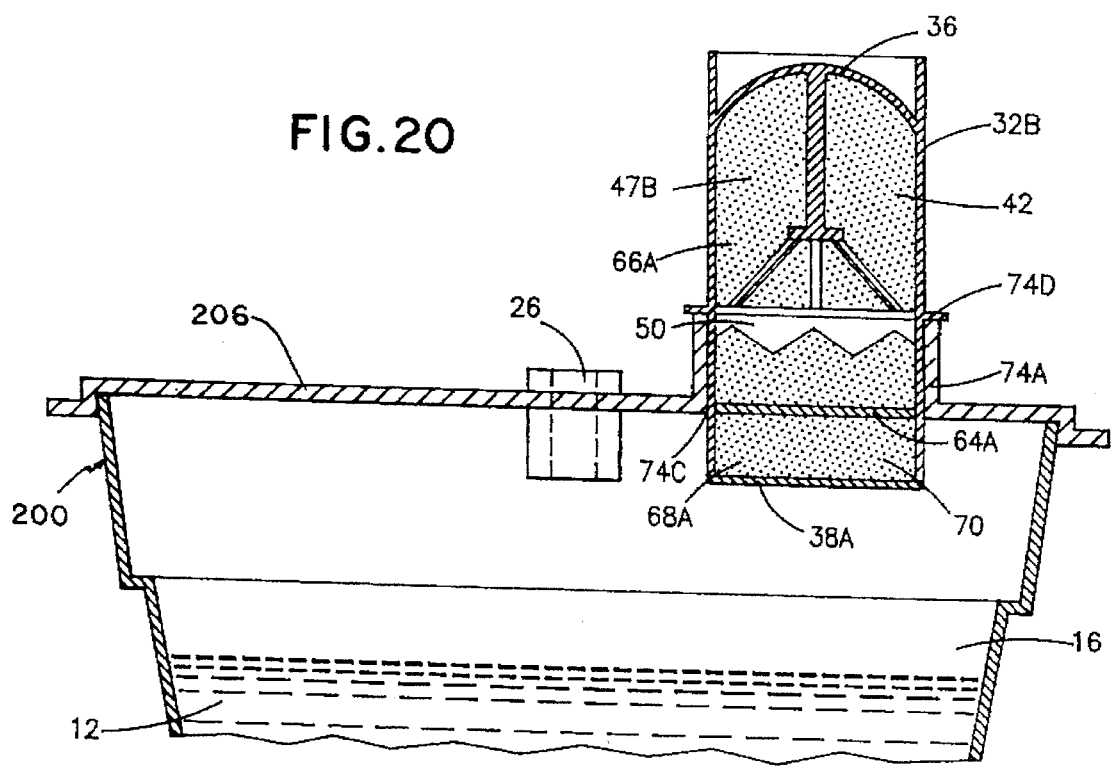

WASTE TREATMENT MATERIAL DISPENSING CANISTER

CROSS REFERRED TO RELATED APPLICATIONS (Claiming Benefit Under 35 U.S.C. 120)

This application is a continuation-in-part application of U.S. application, Ser. No. 07/507,966, filed Apr. 11, 1990, which is a continuation-in-part of application, Ser. No. 215,370 filed Jul. 5, 1988, now abandoned, which is in turn a continuation-in-part of application, Ser. No. 105,875, now abandoned, filed Oct. 7, 1987 by Jack W. Kaufman.

BACKGROUND OF THE INVENTION

This invention relates to a waste treatment material dispensing device; and, more particularly, it relates to a waste treatment material dispensing device for use in connection with the disposal of body waste fluids. Recently, there has been a growing trend in the use of safe waste disposal devices for disposing aqueous body waste fluids such as blood and other fluids drained from patient's body cavities.

Body waste fluids that are drained or drawn from a hospital patient are collected in an operating room or bedside fluid vessel, generally with either a rigid-walled canister or a soft walled plastic fluid vessel that is set into a receptacle mounted to a vacuum machine. Both types of vessels are provided with a lid which has an inlet patient port in turn connected to the patient by a patient line, and further has a vacuum port connected to a vacuum machine by a vacuum line. The lid may also have a drain port from which the body waste fluids are disposed of at a designated disposal area in the hospital before disposal of the vessel itself.

These body waste fluids frequently include harmful components including viruses and other pathogens. During the sealing and discarding process there is a risk that the collected fluids may escape from the vessel and come into contact with personnel. In particular, health care workers are exposed to an increased risk of contracting disease from contact with these pathogens. A common risk factor includes contact with blood and other body fluids escaping from drainage devices. Fluids escape from these drainage devices through splashing or aerosolization during disposal. By way of example, drainage devices frequently have removable covers. As the covers are snapped on and off, body fluids splash, aerosolize, and contaminate the underside of a cover and the surrounding area, thus creating a hazard to health care workers and other patients.

Various measures for reducing the risks of splashing, aerosolization, and contamination have been proposed. By way of example, waste treatment material is released into a drainage device from a reservoir. Gravity then pulls the waste treatment material from the reservoir into body fluids contained within the device, e.g. U.S. patent application Ser. No. 215,370 filed by Kaufman.

There are a number of problems associated with the release of waste treatment material from reservoirs used in drainage devices. A primary problem is associated with a build up of gas pressure within the closed drainage device as body fluids accumulate. The build up of pressure makes it difficult to release the waste treatment material from a reservoir into contact with body fluids in order to immobilize or disinfect the fluids. There exists a need for a device that provides for the dispersion of waste treatment material into a drainage device notwithstanding a build up of pressure within the device.

A second problem involves the lack of interchangability of reservoirs. More particularly, reservoirs may be specific to particular types of drainage devices. There is no way to interchange a reservoir containing one type of waste treatment material with another reservoir containing an alternate waste treatment material from one drainage system to another. Hence, there exists a need for a reservoir that can be utilized in a variety of drainage systems.

Yet a further problem with drainage devices involves the problem of caking. As body waste fluids accumulate in a drainage device splashing occurs. Waste treatment material cakes around a reservoir, thus decreasing the dispersion of the waste treatment material. There exists a need for a waste treatment material dispensing device that provides increased dispersion and decreases caking of waste treatment material.

It is an object of the present invention to solve these and other problems encountered in health care facilities. The present invention targets the thousands of health care facilities who provide drainage systems for use by their patients in the United States and worldwide, and serves these markets by providing a waste treatment material dispensing device that allows for increased dispersion of waste treatment material, that allows for increased safety by providing for decreased spillage and aerosolization of pathogen containing body fluids, that allows for interchangability between different types of drainage systems, and that has a lower manufacturing cost.

SUMMARY OF THE INVENTION

The present invention provides a body waste fluids collecting container for use in the disposal of waste fluids drained from a body cavity of a patient. The collecting container has inlet and outlet ports, a collecting compartment for collecting body waste fluids drained from a patient, and a retaining compartment located within the collecting container. A composition for treating body waste fluids is located within the retaining compartment. A composition consists of a disinfectant, a xerogel, or combination thereof. A removable wall separates the composition from the collecting compartment. An actuator opens the wall and permits release of the composition from the retaining compartment upon actuation.

The invention further provides a waste treatment material dispensing device for use with a waste fluid disposal vessel. The device contains waste treatment material and a container defining a storage volume for holding the waste treatment material. The container is capable of being lockably disposed in a port located on the waste fluid disposal vessel, and has an exit port open to the fluid disposal vessel. A wall covers the exit port and temporarily retains waste treatment material. An actuator is provided on the container for releasing the waste treatment material into a storage volume of the vessel.

It is yet another object of the invention to provide a body waste fluids system which both solidifies body waste fluids in a collection vessel and destroys or at least deactivates infectious agents within the vessel in preparation for disposal. The system includes a container for holding at least one hydrophilic xerogel composition in a free-flowing powder form and a release means operatively associated with the container for allowing the xerogel composition to exit from the container into contact with the body waste fluids, whereupon the xerogel composition mixes and interacts with the body waste fluids so as to immobilize the body waste fluids into a solidified mixture, or gel, so that the collection vessel along with the solidified mixture can be efficiently disposed of. The container can also optionally hold a disinfectant powder generally in a compartment separate from the xerogel. The container can be connected to the lid of the collection vessel, and the xerogel or the xerogel and the disinfectant allowed to exit the container so as to come into contact with the body waste fluids in the vessel by manual operation of a release system mounted to the container.

The objects and features of the present invention, other than those specifically set forth above, will become apparent in the detailed description of the invention set forth below.

BRIEF DESCRIPTION OF THE DRAWINGS

FIG. 4 is a partial top plan view of a lid of a waste fluid collection vessel of FIG. 1 showing a port, and top wall and prongs of a waste material dispensing device.

FIG. 5 is a partial top plan view of a lid of a waste fluid collection vessel of FIG. 1, and top wall, prongs, and an interior wall of a waste material dispensing device.

FIG. 19 is a side sectional view showing a waste treatment material dispensing device having a xerogel where the dispensing device is lockably secured to a port located on a lid of a medical waste fluids collection vessel.

FIG. 20 is a side sectional view showing a waste treatment material dispensing device having a xerogel and disinfectant where the dispensing device is lockably secured to a port located on a lid of a medical waste fluids collection vessel.

DETAILED DESCRIPTION OF THE INVENTION

Figure 1:
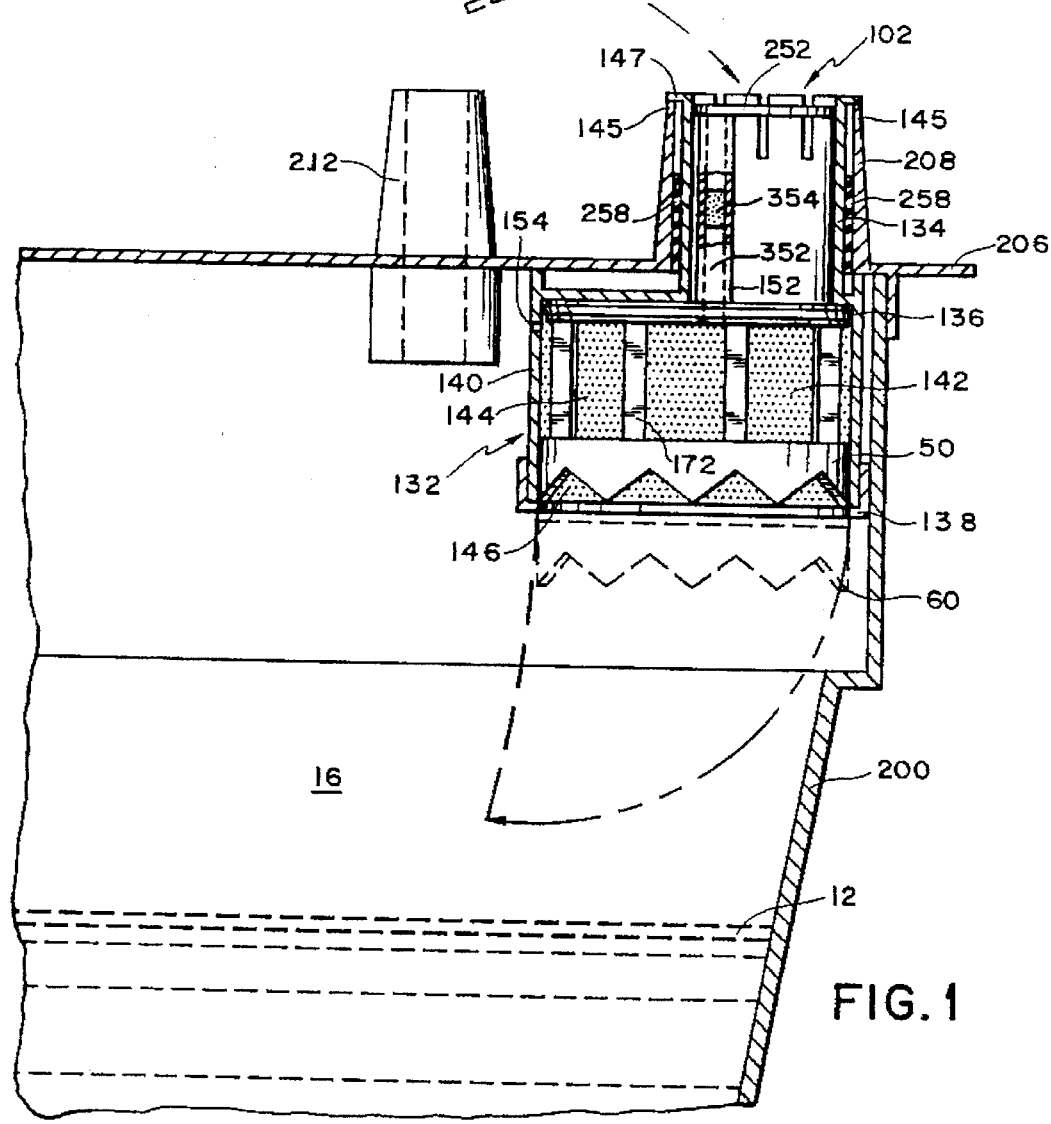
FIG. 1 is a cross sectional view of a waste treatment material dispensing device located in a closed waste fluid disposal vessel.

FIG. 1 is a cross sectional view of waste treatment material dispensing device 102. Device 102 is used with closed waste fluid disposal vessel 200. Device 102 is of a size and shape to be secured in port 208 disposed on lid 206, and is commonly used to retrofit vessels produced by a variety of manufacturers.

Device 102 consists of container 132. Container 132 is lockably disposed in drainage port 208 (FIGS. 1, 2, 4, and 5) and includes upper and lower walls 136 (FIGS. 1, 2, and 5) and 138 (FIG. 1), respectively, transverse to cylindrical neck wall 134 and cylindrical body wall 140. Cylindrical body wall 140, upper wall 136, and lower wall 138 together define storage volume 142 (FIGS. 1 and 2) for holding waste treatment material 144. Storage volume 142, in a preferred embodiment, is configured as a cylinder having a generally vertical axis. Volume 142 holds a hydrophilic xerogel composition 42 (FIGS. 6, 8, 15, 16, 18–22, and 24–26) in powder form, the powder being, preferably, a free-flowing powder, a disinfectant 70 (FIGS. 6, 8, 15, 20, 24, and 25), or combination thereof. Xerogel 42 includes at least one hydrophilic polymer. The present invention further contemplates the use of a liquid xerogel composition 42, disinfectant 70, or combination thereof.

Container 132 has exit port 146 (FIG. 1) open to storage volume 16. Storage volume 16 is disposed within fluid disposal vessel 200. A removable wall 138 covers exit port 146. Wall 138 retains waste treatment material 144 in storage volume 142 when wall 138 is in a closed position. In one embodiment, wall 138 is removably mounted, for example, by gluing to cylindrical body wall 140 at exit port 146. In yet another embodiment, wall 138 comprises a frangible material. The present invention contemplates that wall 138 comprises a removable cap (not shown).

Container 132 includes cylindrical neck wall 134 (FIGS. 1, 2 and 3) extending above storage volume 142. Neck wall 134 terminates in a top portion 145. Top portion 145 contains cantilevered prongs 147 (FIGS. 1, 2, 3, 4, 5, 9, and 10) disposed on neck wall 134. It will be appreciated that prongs 147 allow device 102 (FIGS. 1, 2, and 3), and device 106 (FIGS. 9 and 10), respectively, to be lockably disposed in port 208. At least two cantilevered prongs 147 are disposed on neck wall 134 for lockably securing devices 102, 106 to port 208. In a preferred embodiment, eight cantilevered prongs 147 are disposed on neck wall 134.

Neck wall 134 is optionally tapered inwardly so as to be adapted for a press fit, that is a friction fit with drainage port wall 208 (not shown). In this embodiment, prongs 147 are optional. In yet another embodiment, neck wall 134, upper wall 136, or a combination thereof, is secured to container 200, or lid 206 with an adhesive.

An actuator is disposed on container 132 for releasing waste treatment material 144 into storage volume 16. The actuator opens wall 138 upon actuation, and gravity assists in the discharge of waste treatment material 144 into storage volume 16.

Figure 2:
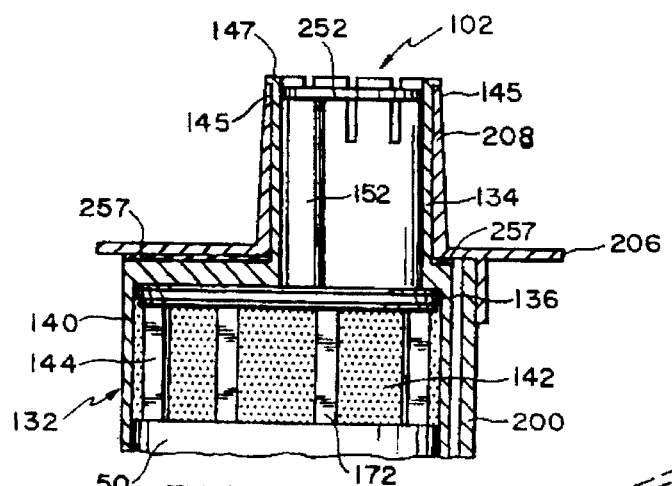
FIG. 2 is an exploded cross sectional view of a waste treatment material dispensing device of FIG. 1 having a sealing means interposed between a port on a closed waste fluid disposal vessel lid and the device.

By way of example, an actuator comprises punch head 50 (FIGS. 1, 2, 9, and 10). Punch head 50 has a plurality of protuberances 60 disposed on head 50 for opening wall 138. Punch head 50 is slidingly disposed in container 132. In a preferred embodiment, protuberances 60 are disposed on the perimeter of head 50. Punch head 50 is connected to wall 136 by rods 172 (FIGS. 1 and 2). Even though the present invention contemplates that a variety of connections may be utilized between wall 136 and head 50, in a preferred embodiment eight rods 172 connect punch head 50 to wall 136.

Where utilized, protuberances 60 are, preferably, partially disposed around the perimeter of head 50 so that upon depression, punch head 50 partially opens wall 138. Where wall 138 comprises a frangible material 300 (FIGS. 1, 9, and 10), e.g. a foil, paper, and the like, punch head 50 penetrates the frangible material creating flap 300 that is partially attached to container 132 (FIGS. 1 and 10).

Figure 10:
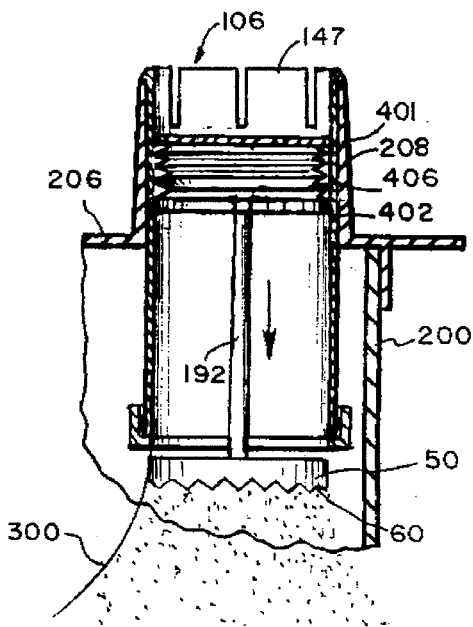
FIG. 10 is a side sectional view of a waste material dispensing device with a bellows in an activated position.

As illustrated in FIGS. 1 and 10, by way of example, a means for depressing a punch head actuates movement of punch head 50 in a downward direction causing protuberances 60 to open wall 138, or frangible material 300. In one embodiment, a means for depressing a punch head consists of connecting rod 152 and movable wall 252 (FIG. 1 and 2). Connecting rod 152 responds to the movement of movable wall 252. Generally, movable wall 252 is depressed causing a downward movement of punch head 50. The downward movement of punch head 50 causes protuberances 60 to open wall 138. Preferably, connecting rod 152 is fixed to wall 252.

As illustrated in FIG. 1, connecting rod 152 may have optional air vent escape 352 disposed within rod 152. Air vent escape 352 allows for venting of gases emanating from waste fluids 12 in storage volume 16. In one embodiment, air vent escape extends from wall 252, at which point it is open to the surrounding environment, through wall 138, at which point it is open to storage volume 16 (FIG. 1).

In another embodiment, air vent 154 (FIG. 1) is located below wall 136. Air vent 154 allows for air pressure that builds up within storage volume 16 to be released. An optional air filter 354 is disposed within air vent escape 152.

Figure 3:
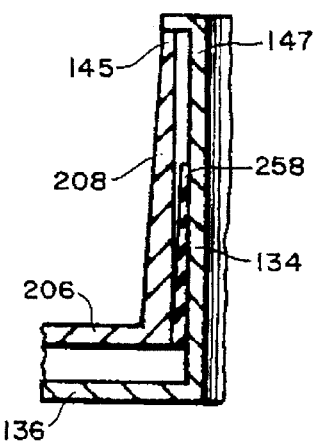
FIG. 3 is an exploded cross sectional view of a neck of waste treatment material dispensing device of FIG. 1 and a port located on a lid located on a closed waste fluid disposal vessel.

Waste treatment material dispensing device 102, 104, 106, as well as other embodiments of the invention, optionally comprise a sealing means 257, 258 (FIGS. 1, 2, and 3). Sealing means include gels, waxes, silicone, rubber, other suitable sealing material, or combination thereof. By way of example, sealing means 257, 258 include a gasket. Sealings means 257 is interposed between container 132 and said waste fluid disposal vessel 200 in one embodiment (FIG. 2). As viewed in FIGS. 1 and 3, sealing means 258 is interposed between port 208 and container 132.

Figure 8:
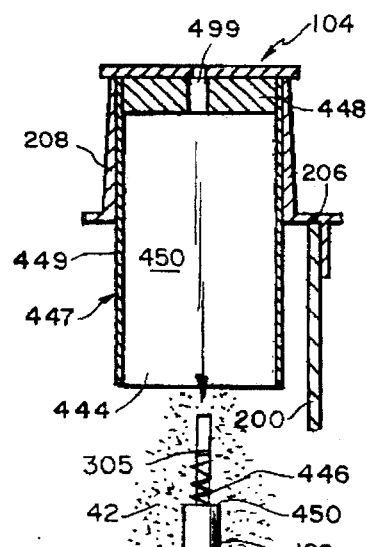
FIG. 8 is a exploded side sectional view of a waste material dispensing device as shown in FIG. 6 in an activated position.
Figure 6:
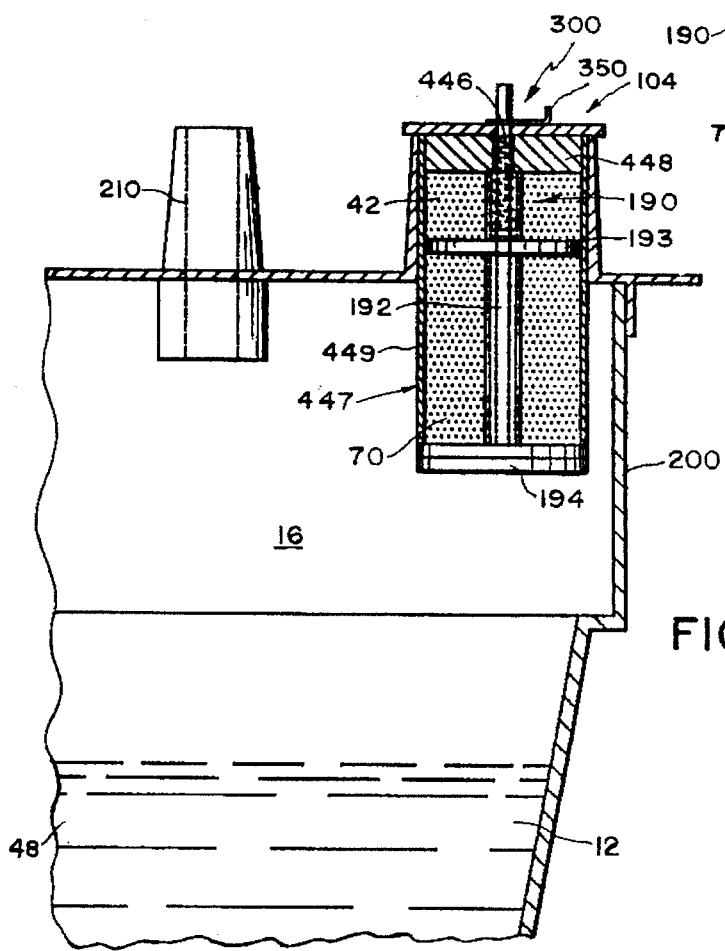
FIG. 6 is a side sectional view of a waste fluids collection vessel and waste material dispensing device biased in an ejection direction and in an inactive position.

Waste treatment material device 104 contains an actuator 190 for propelling waste treatment material 144 from device 104 into storage volume 16 (FIGS. 6 and 8). Actuator 190 is biased in an ejection direction. As illustrated in FIGS. 6 and 8, actuator 190 comprises plunger rod 192. Plunger rod 192 has at least one release head responsive to movement by plunger rod 192. In one embodiment, plunger rod 192 has an upper release head 193, and a lower release head 194. Lower release head 194 retains waste treatment material in container 447 prior to actuation.

Container 447 has upper wall 448. Upper wall has aperture 499 (FIG. 8). Container 447 is generally cylindrically shaped with cylindrical wall 449, wall 448, and release head 194 forming storage volume 450. Storage volume 450 is used to retain waste treatment material 144. As illustrated in FIG. 6, an upper portion of storage volume 144 may be used to store xerogel 42, and a lower portion may be used to store disinfectant 70. Exit port 444 is disposed opposite wall 448.

Actuator 190 is in an inactive position when release head 194 abuts wall 447 (FIG. 6). Actuator 190 is in an activated position is when release head 194 is positioned below exit port 444 after having been propelled from connection with wall 449 into storage volume 16 of canister 200 (FIG. 8). When activation is achieved, waste treatment material, e.g. xerogel composition 42, disinfectant 70, or combination thereof, is released from storage volume 450 for movement into storage volume 16 for mixture therein with body waste fluids 12. The mixture of the waste treatment material and fluids 12 results in the formation of gel 48, a disinfected fluid 12, or combination thereof.

As illustrated in FIGS. 6 and 8, device 104 contains a means for biasing plunger rod 192 in an ejection direction. A means for biasing plunger rod 192 includes, by way of example, spring 446 (FIGS. 6 and 8). Spring 446 rests in aperture 449 against wall 448, and against edge 450 on plunger rod 192 when actuator 190 is in an inactive position. Spring 446 biases rod 192 in an ejection direction, e.g. in a direction toward storage volume 16 and toward contact with fluids 12.

Figure 7:
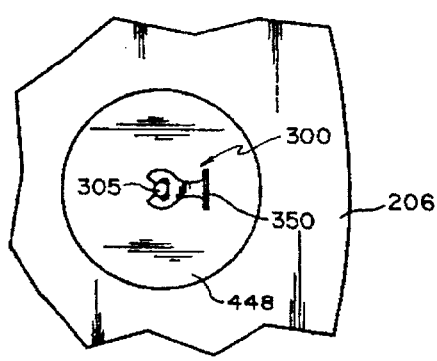
FIG. 7 is a partial top plan view of a lid of the device of FIG. 6 showing, a top wall of a waste material dispensing device, a rod, and a trigger in an inactive position.
Figure 11:
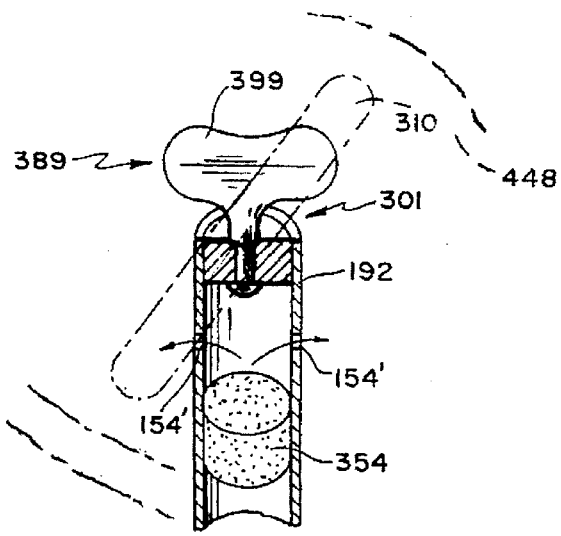
FIG. 11 is a perspective view of a trigger for use with a waste material dispensing device where the trigger has a rotatable winged wall.
Figure 12:
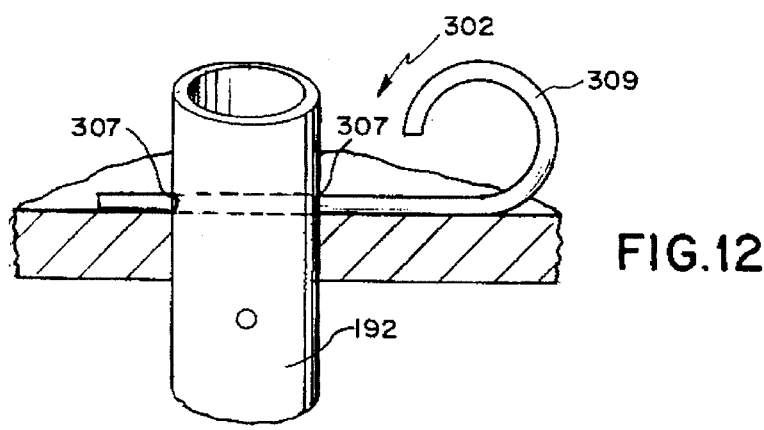
FIG. 12 is a perspective view of a trigger for use with a waste material dispensing device where the trigger consists of an aperture located in a plunger rod and a pin removably disposed within the aperture.

A trigger 300 (FIGS. 6 and 7), 301 (FIG. 11), 302 (FIG. 12) is provided for releasing said plunger rod 192 in an ejection direction. As viewed in FIGS. 8, trigger 300 comprises a grove 305 disposed on plunger rod 192, and clasp 350. In an inactivated position, clasp 350 rests in grove 305 (FIG. 6 and 7). Clasp 350 is removably disposed in grove 305 such that removal of clasp 350 activates actuator 190. As viewed in FIG. 12, trigger 302 comprises an aperture 307 disposed on plunger rod 192, and a pin 309 disposed within aperture 307 when plunger rod 192 is in an inactive position. Pin 309 is removably disposed in aperture 307 such that removal of pin 309 results in activation. As viewed in FIG. 11, trigger 301 comprises aperture 310 disposed on wall 448, and a winged pin 389 rotatably disposed within rod 192. Winged pin 389 comprises winged wall 399. In an inactive position winged wall 399 rests against wall 448. Rotation of winged pin 389 so that wall 399 is substantially parallel to aperture 310 results in activation of the actuator as plunger rod 192 moves down into storage volume 450, and volume 16. Rod 192 optionally contains filter 354 in this embodiment. Rod 192 can also optionally contain air vent 154'.

Figure 9:
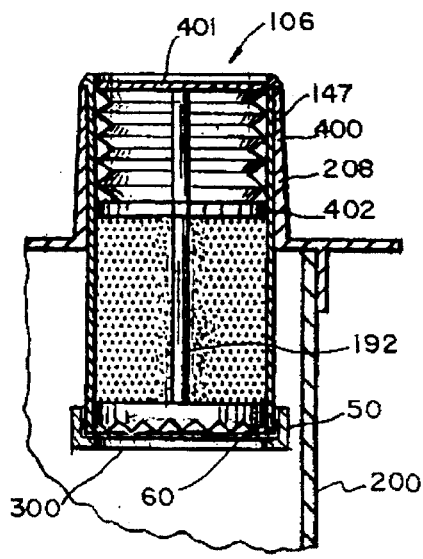
FIG. 9 is a side sectional view of a waste material dispensing device with a bellows in an inactive position.

As illustrated in FIGS. 9 and 10, waste treatment material dispensing device 106 comprises an actuator with bellows 400. Plunger rod 192 is disposed within bellows 400. Punch head 50 is responsive to movement of plunger rod 192. Movement of plunger rod 192 is accomplished by depressing wall 401 from an inactive position as viewed in FIG. 9 to an activated position toward lower wall 402 as viewed in FIG. 10. Wall 401, wall 402, or a combination thereof may be vented as appropriate to release air build up. As previously discussed, punch head 50 has a plurality of protuberances 60 disposed thereon for opening wall 300, and is slidingly disposed in container 447.

As illustrated in FIGS. 1, 6, 13, 14, and 18–23, a closed body waste fluids collection container, e.g. canister 200, vessel 204 with lid 206, or combination thereof, is used in the disposal of waste fluids 12 drained from a body cavity of a patient (not shown), The container may have an inlet port 210, and an outlet port 218 disposed thereon. A collecting compartment, e.g. storage volume 16 collects body waste fluids 12. A composition, e.g. waste treatment material 144, is disposed within a reservoir, e.g. device 102 (FIGS. 1 and 2), 104 (FIGS. 6 and 8), 106 (FIGS. 9 and 10), 32 (FIGS. 15–17), 32A (FIGS. 18–19), 32B (FIG. 20), or other embodiment described herein. The reservoir is disposed on the container. A separation, e.g. 38 (FIGS. 15, 16, 18, and 19), 64 (FIG. 16 and 17), 138 (FIG. 1), 300 (FIG. 9 and 10) is interposed between the composition and the collecting compartment. The separation retains the composition within the reservoir while in an inactive position. An actuator, as described above, opens the separation upon activation. The composition discharges into the collecting compartment upon actuation of said actuator.

Figure 13:
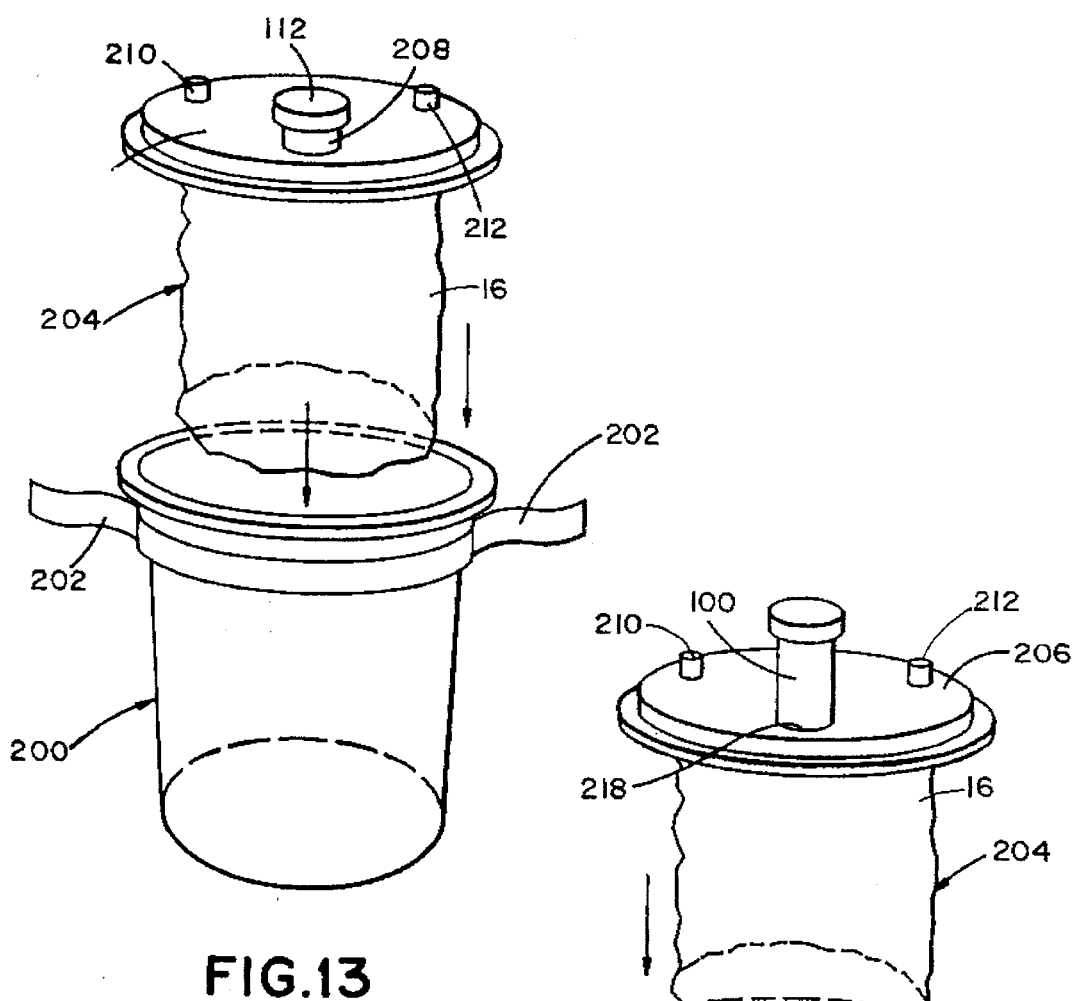
FIG. 13 is a perspective view of a medical collection vessel having a flexible plastic wall with an integral lid and having a drainage port, where the flexible plastic wall is being inserted into a permanent hard-walled support container.
Figure 14:
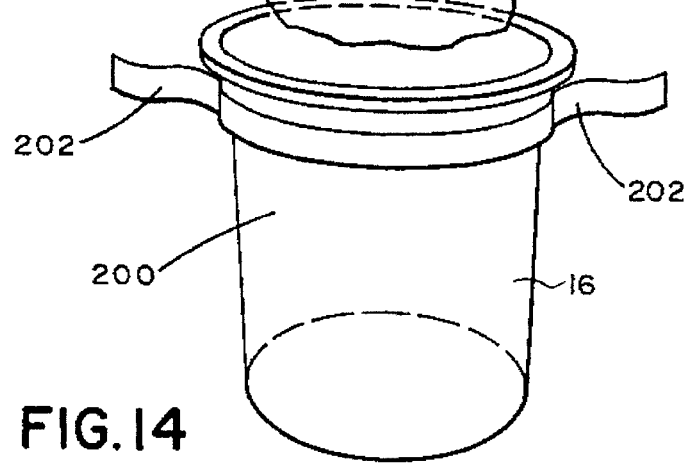
FIG. 14 is a perspective view of a medical collection vessel having a flexible plastic wall with an integral lid where a waste treatment material dispensing device is located on the lid.

FIGS. 13 and 14 illustrate a flexible-walled plastic collection vessel 204 with a lid 206 used to collect body waste fluids 12 (not shown). Hard-walled canister 200 with removable canister lid 206 is also used to collect body waste fluids 12. As used herein, the terms, medical fluids vessel, closed body waste fluids collection container, collection vessel, collection container, and canister, are used interchangeably. Lid 206 is integral with flexible walled collection vessel 204 by being fixed thereto in one embodiment. Lid 206 has a drainage port 208 with a drainage port cap 112, a patient inlet port 210, and a vacuum port 212. Vessel 204 is in operation set into a medical hard-walled canister 200, which is secured by mounts 202 to a vacuum machine (not shown). When vessel 204 is full, it is lifted, along with lid 206, from canister 200 and disposed of in the manner described for the disposal of body waste fluids earlier. Canister 200, being dry and uncontaminated, is retained. Various waste treatment dispensing devices described herein can all be used with flexible-walled collection vessel 204 by placement of the named containers into vessel 204 through drainage port 208, or aperture 218. Waste treatment dispensing container 32A, illustrated in FIGS. 18 and 19, waste treatment dispensing container 32B illustrated in FIG. 20, waste treatment material dispensing device 102 illustrated in FIGS. 1 and 2, waste treatment material dispensing device 104 illustrated in FIGS. 6 and 8, and waste treatment material dispensing device 106 illustrated in FIGS. 9 and 10, are also insertable into storage volume 16 through drainage port 208, or aperture 218. In the just mentioned containers, when insertion is made and waste treatment material 144 discharged, body waste fluids 12 are immobilized in the form of solidified mixture, or gel in the manner described. In addition, where present, disinfectant 70 also destroys or deactivates infectious agents in body waste fluids 12.

FIG. 14 also illustrates a flexible-walled plastic collection vessel 204 used to collect body waste fluids 12. vessel 204 has an integral lid 206 which has an aperture 218 through which is sealably mounted a container 100 analogous to container 32, waste treatment dispensing container 32A, waste treatment material dispensing device 102 illustrated in FIGS. 1 and 2, waste treatment material dispensing device 104 illustrated in FIGS. 6 and 8, and waste treatment material dispensing device 106 illustrated in FIGS. 9 and 10. Vessel 204 is in operation set into a medical hard-walled canister 200 which is secured by mounts 202 to a vacuum machine 234 (not shown). When vessel 204 is full, container 100 is manually operated in the manner described for these systems. After immobilization of body waste fluids 12 in the form of solidified mixture, or gel 48. Vessel 204 is lifted along with its lid 206 and container 100 from canister 200 and disposed of in the manner described earlier for the disposal of body waste fluids where body waste fluids 12 are immobilized in the form of solidified mixture, of gel, 48 and/or disinfected.

Canister 200 generally defines a storage volume 16. A lid 206 is removably secured to canister 200 in one embodiment. Canister 200 and canister lid 206 may be made of a rigid plastic material. Lid 206 has a patient inlet port 210 in turn connected to the patient by patient line and a vacuum port 212 connected to vacuum line. Canister lid 206 is provided with an aperture 218. Lid 206 may be integral with flexible walled collection vessel 204, or may be removably connected thereto.

Figure 15:
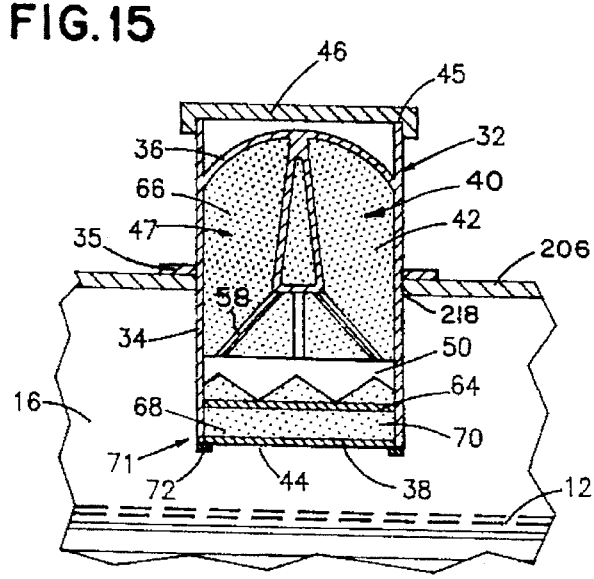
FIG. 15 is a side sectional view showing a waste treatment material dispensing device having xerogel and a disinfectant shown in an inactive mode.
Figures 16, 17:
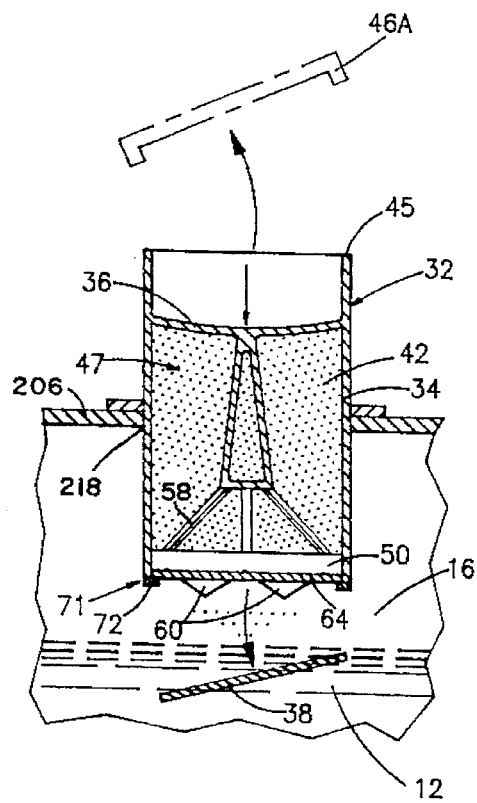
FIG. 16 is a side sectional view showing a waste treatment material dispensing device having xerogel and a disinfectant shown in a partially activated mode.
FIG. 17 is a side sectional view showing a waste treatment material dispensing device having xerogel and a disinfectant shown in a fully activated mode.

FIGS. 15, 16, and 17 illustrate a container 32 mounted to a canister 200 (FIGS. 13 and 14) having a canister lid 206 and an aperture 218. Container 32, sealably positioned in aperture 218 by a sealing ring 35, includes a continuous generally upright wall 34, and opposed upper and lower walls 36 and 38, respectively, transverse to cylindrical wall 34 that together define a sealed chamber 40 configured as a cylinder having a generally vertical axis holding at least one hydrophilic xerogel composition 42 in powder form, the powder being a free-flowing powder, a disinfectant 70, or combination thereof. Xerogel 42 includes at least one hydrophilic polymer. Chamber 40 has an exit port 44 with lower wall 38 being removably mounted, for example, by gluing to cylindrical wall 34 at exit port 44. Lower wall 38 is a thin, penetrable material such as foil, in one embodiment. Container 32 includes a top portion with a cylindrical side wall 34 extending above domed upper wall 36 terminating in a top edge 45. A removable cap 46, 46A is positioned around top edge 45.

A release device 47, also referred to herein as an actuator, operatively associated with container 32 allows xerogel composition 42, a disinfectant 70, or combination thereof, to exit, discharge, or outflow, by force of gravity from chamber 40 into contact with body waste fluids 12. Xerogel composition 42 mixes with body waste fluids 12 so that xerogel composition 42 absorbs the aqueous portion of body waste fluids 12 resulting in an insoluble gel in which the remainder of the fluids are absorbed and immobilized resulting in a solidified, or gel like, mixture 48.

Release device 47 includes a punch head 50 slidably mounted in chamber 40 and a generally vertical connecting rod 52 (FIG. 17) positioned at the axis of chamber 40 and having upper and lower ends 54 and 56, respectively, upper end 54 being flexibly connected to the axial center of domed upper wall 36. Rod 52 is configured as a pair of semi-cylindrical walls spaced slightly apart but can optionally be a single straight piece. Upper wall 36 is domed, or dome-shaped, and is integrally and flexibly connected around its circular peripheral edge to the inner surface of cylindrical wall 34. Domed upper wall 36, connecting rod 52, and punch head 50 are movable by exertion of downward manual pressure against upper wall 36, after removal of cap 46, from an inactive position, as illustrated by way of example in FIG. 15, directly to an activated positioned (not shown), or to a semi-activated as illustrated in FIG. 16, and then to a fully activated position as illustrated in FIG. 17. Domed upper wall 36 is convex upwardly in the inactive position and is convex downwardly in the activated position. The inactive position is when punch head 50 is spaced above removable lower wall 38, and the activated position is when punch head 50 is positioned below exit port 44 after having punched lower removable wall 38 from connection with container 32 and into storage volume 16 of canister 200 at which time xerogel composition 42, disinfectant 70, or combination thereof, is released from chamber 40 for movement into storage volume 16 for mixture therein with body waste fluids 12 resulting in the formation of gel 48, a disinfected fluid 12, or combination thereof.

Punch head 50 is configured as an interior cylindrical wall slidably mounted within and axially aligned with cylindrical chamber 40. Connecting rod 52 includes six equally spaced support rods 58 extending downwardly at an angle between lower end 56 of connecting rod 52 and punch head 50. Container 32, domed wall 36, support rods 58, punch head 50, and connecting rod 52 are integral and made of a flexible plastic to allow hinged movements between the top of connecting rod 52 and domed upper wall 50 and between the circumference of domed upper wall 36 and the interior of container 32. Chamber 40 holding xerogel composition powder 42, disinfectant 70, or combination thereof, includes areas above and below support rods 58. When punch head 50 is moved to the activated position, the portion of xerogel composition 42, disinfectant 70, or combination thereof, positioned in chamber 40 above punch head 50 passes downwardly between support rods 58 as the portion of xerogel composition 42, disinfectant 70, or combination thereof, exits downwardly through exit port 44.

Removable lower walls 38, 64 are configured as a flat surface and are made of a penetrable material such as foil. Punch head 50 includes a plurality of downwardly directed piercing tips 60 located around the bottom side of the interior cylindrical wall of punch head 50, in one embodiment, wherein when punch head 50 is moved from the inactive position to the activated position, piercing tips 60 penetrate lower wall 38 so as to aid in the removal of lower wall 38 from sealable connection with container 32 by the downward force from punch 50.

A release device 47 is mounted to container 32. A removable intermediate sealing wall 64 is located within chamber 40 between and lateral to upper and lower chamber walls 36 and 38 forming from chamber 40 upper and lower compartments 66 and 68, respectively, wherein upper compartment 66 contains xerogel powder composition 42 in the form of a powder, the powder being free flowing powder. Lower compartment 68 containing disinfectant 70, composition 42, or a combination thereof.

Domed upper wall 36, connecting rod 52, and punch head 50 are movable by exertion of downward force manual pressure against upper wall 36, after removal of cap 46, from an inactive position as illustrated in FIG. 15 to a semiactive position as illustrated in FIG. 16 and then movable to a fully activated position as illustrated in FIG. 17. The inactive position is when punch head 50 is located above exit port 44. The semiactivated position is when said punch head 50 is positioned immediately above exit port 44 after having caused removable lower wall 38 to be moved from connection with container 32 via manual pressure applied to punch head 50 causing intermediate wall 64 to be moved to exit port 44, so that disinfectant 70 is released from lower compartment 68 for movement into storage volume 16 of canister 200 for mixture therein with body waste fluids 12 resulting in the substantial destruction or at least deactivation of infectious agents in body waste fluids 12 in storage volume 16. The fully activated position is when punch head 50 has been moved downward by further manual pressure at upper wall 36 for positioning below exit port 44 after having punched intermediate wall 64 from connection with container 32 into storage volume 16 of canister 200, so that xerogel composition 42 is released from upper compartment 66 into storage volume 16 of canister 200 for mixture therein with the now sterilized body waste fluids 12 resulting in the formation of a solidified mixture, or gel, in storage volume 16.

Figure 18:
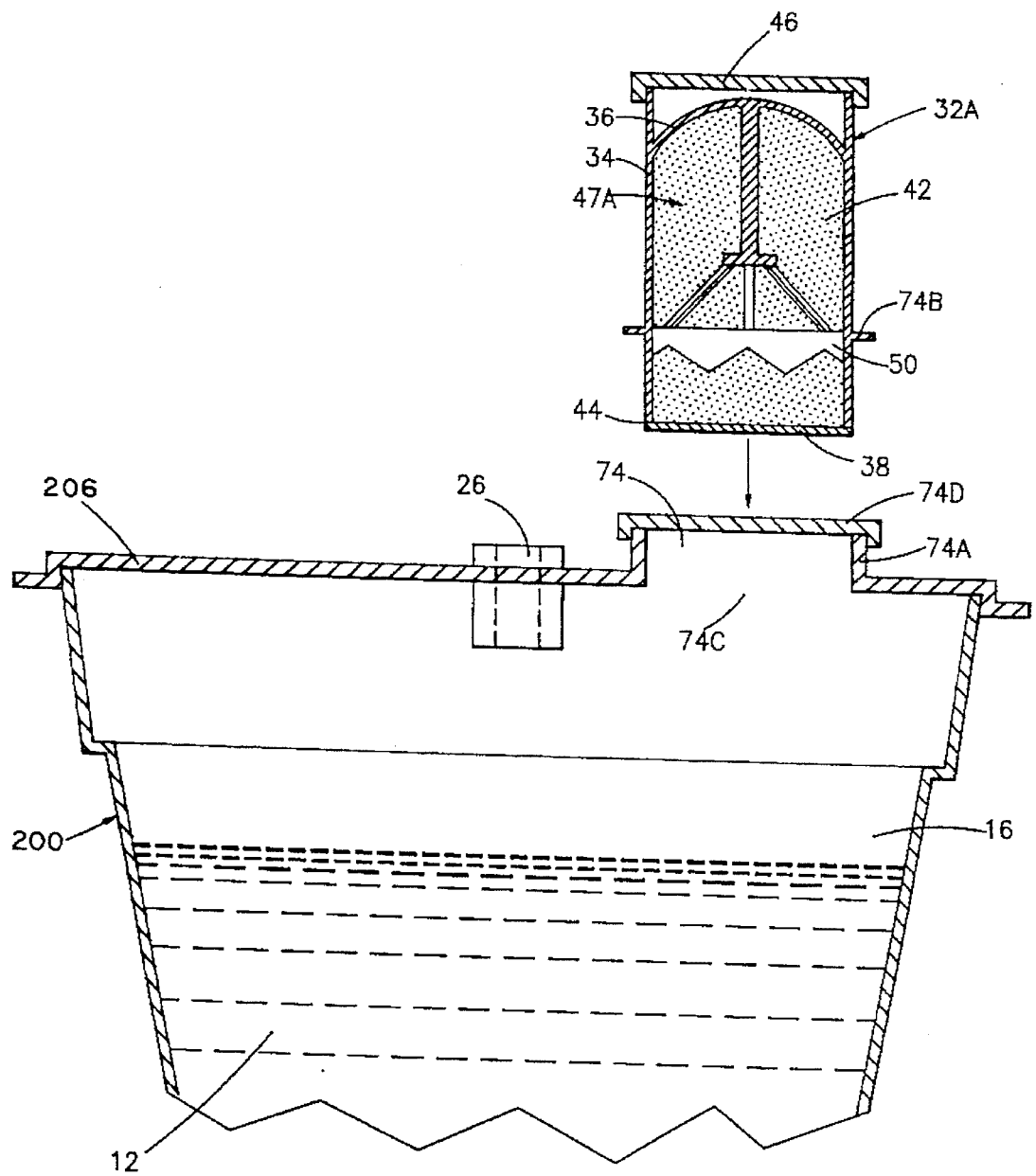
FIG. 18 is a side sectional view showing a waste treatment material dispensing device having a xerogel in position to be lockably secured to a port located on a lid of a medical waste fluids collection vessel.

Independent container 32A is separate and apart from canister lid 206 but otherwise mutatis mutandis is like container 32. FIG. 18 illustrates independent container 32A positioned for insertion into canister 200 through preexisting drain port 74 having an upright cylindrical wall 74A. The diameter of container 32A is slightly less than the diameter of drain port 74. A cylindrical stop ring 74B is flanged outwardly from container wall 34A. Insertion of container 32A into drain port 74 after removal of drainage port cap 74D, shown in FIG. 19 in phantom line in the removed position as cap 74E, takes place after body waste fluids 12 have accumulated in storage volume 16. FIG. 19 illustrates independent container 32A positioned in drainage port 74 in a mounted position with canister lid 206 with stop ring 74B settled against port wall 74A ready for manual operation from the inactive position as shown and described relative to the activated position. Exit port 44 of container 32A is aligned with the aperture 74C of drainage port 74 opening to storage volume 16 of canister 200. Cylindrical wall 34A is optionally tapered inwardly so as to be adapted for a press fit, that is a friction fit with drainage prot wall 74A.

As illustrated in FIGS. 20, canister 200 has a canister lid 206 the same as canister lid 206 as hereinabove described. An independent container 32B holds xerogel composition 42 in an upper compartment 66A and disinfectant 70 in a lower compartment 68A and a removable lower wall 38A is removably secured to the exit port of container 32B. Independent container 32B is separate and apart from canister lid 206 but otherwise mutatis mutandis is like container 32A of FIG. 19. FIG. 20 illustrates independent container 32B having been inserted into canister 200 through pre-existing drain port 74 of canister lid 206 ready for manual operation from an active position to a semiactivated and activated positions. The diameter of container 32B is slightly less than the diameter of drain port 74. Insertion takes place after the body waste fluids 12 have accumulated in storage volume 16.

As illustrated in FIGS. 15–17, a locking device 71 is connected to container 32 at exit port 44 for holding lower wall 38 in position in the inactive position and is also for holding intermediate wall 64 in position at exit 44 when the waste treatment dispensing device is in the semiactivated position. Locking device 71 includes a resilient, or biasable, ring 72 secured around the circumference of exit port 44 and extending radially inwardly so as to provide a circular support upon which is positioned lower wall 38 or intermediate wall 64 in the inactive or semiactivated positions. Biasable ring 72 flexes downwardly when sufficient pressure is applied upon it during the downward movement of release device 47 so as to release lower wall 38 after which release intermediate wall 64 continues to move downwardly until resistance is met by biasable ring 72 at which time the manual pressure is lifted briefly until disinfectant 70 has time to mix with body waste fluids 12 after which the system is manually moved to the fully activated position so that intermediate wall 64 is pressured downwardly so as to cause biasable ring 72 to flex downwardly sufficiently for intermediate ring 64 to pass into storage volume 16 and release xerogel composition 42 into storage volume 16 for mixing with sterilized body waste fluids 12 resulting in the subsequent formation of sterilized solidified mixture or gel.

Figure 21:
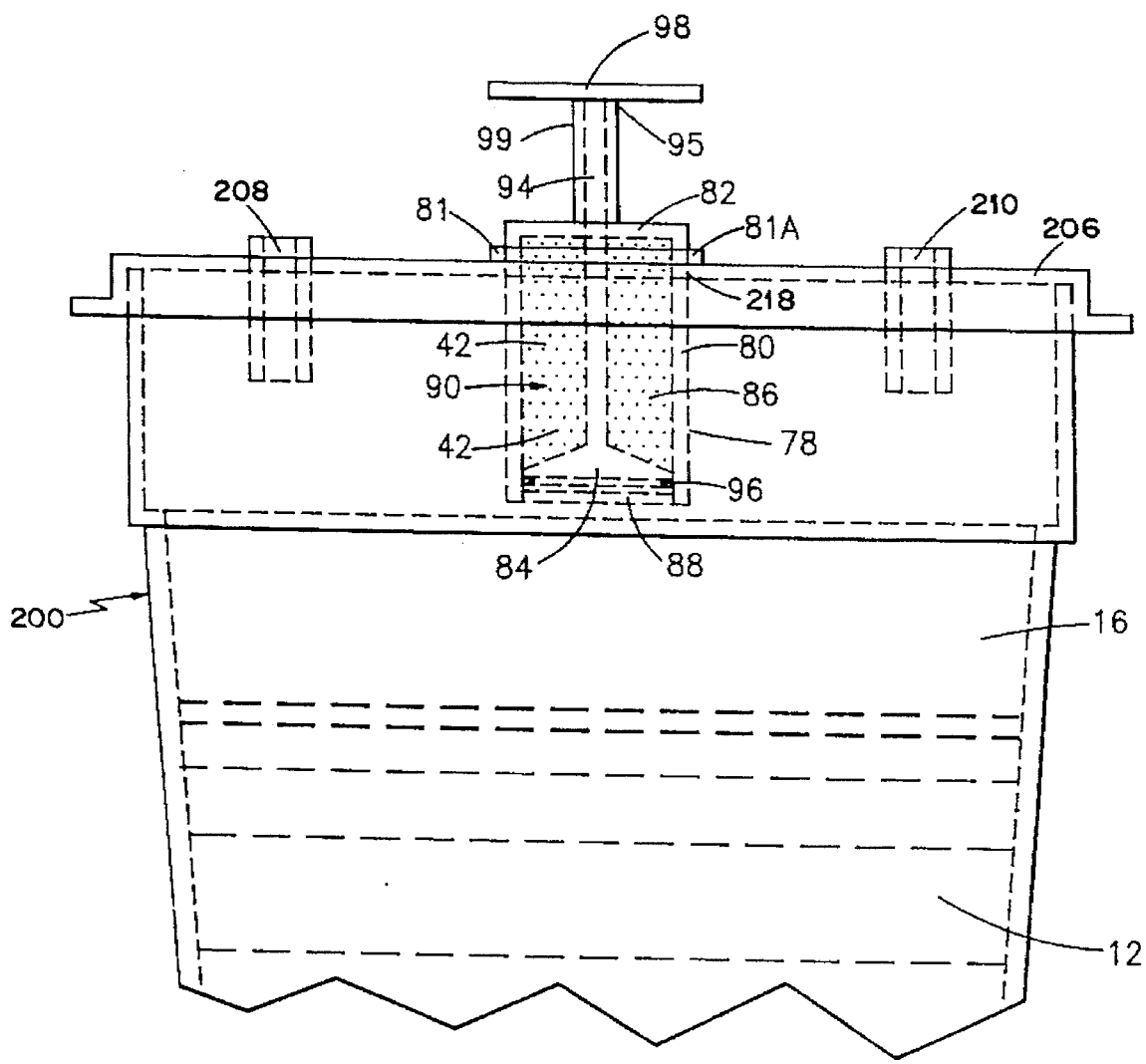
FIG. 21 is an elevational view showing a waste treatment material dispensing device located on a medical waste fluids disposal vessel lid having a plunger in an inactive position.
Figure 22:
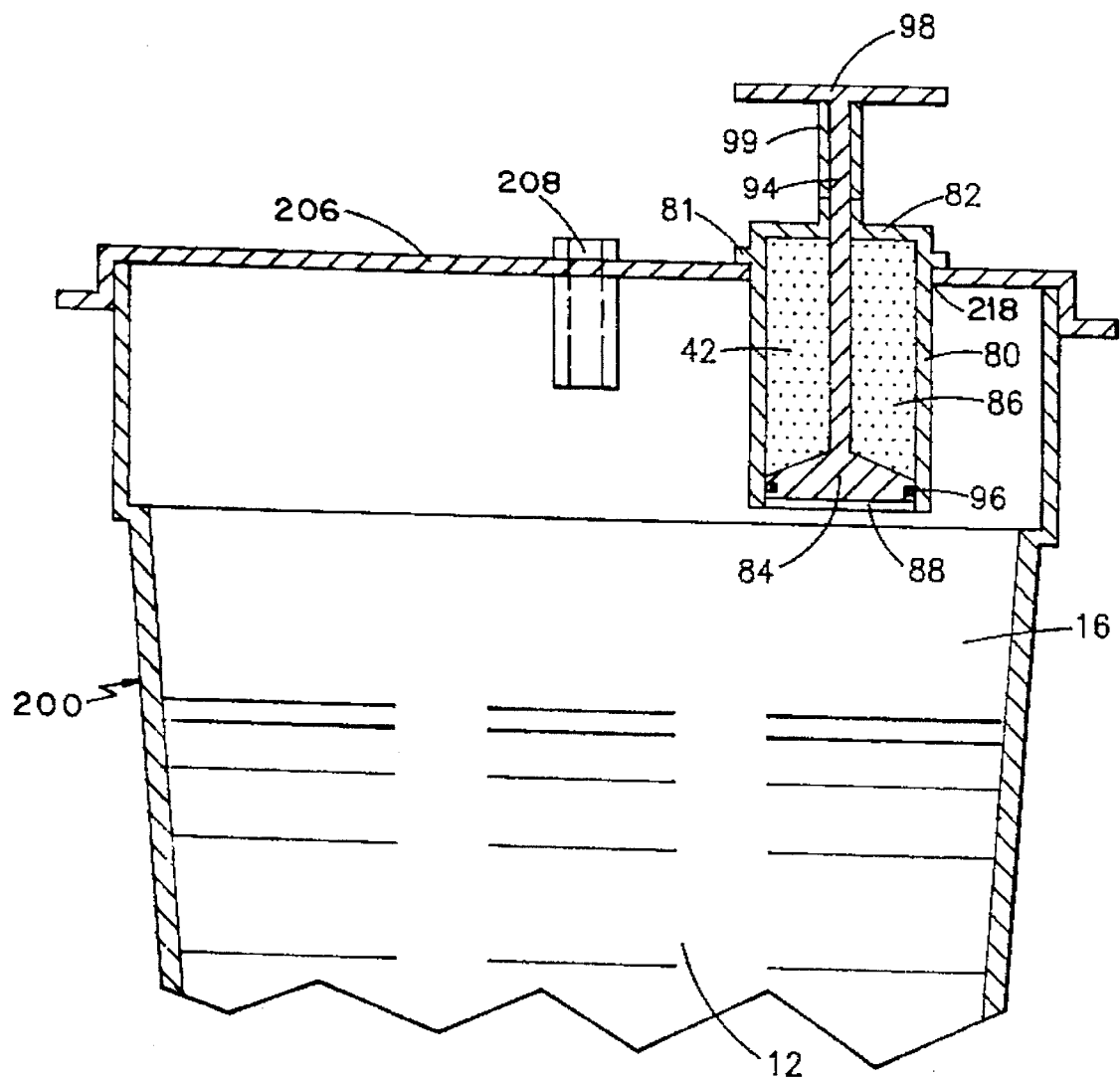
FIG. 22 is an elevational view showing a waste treatment material dispensing device having xerogel powder.
Figure 23:
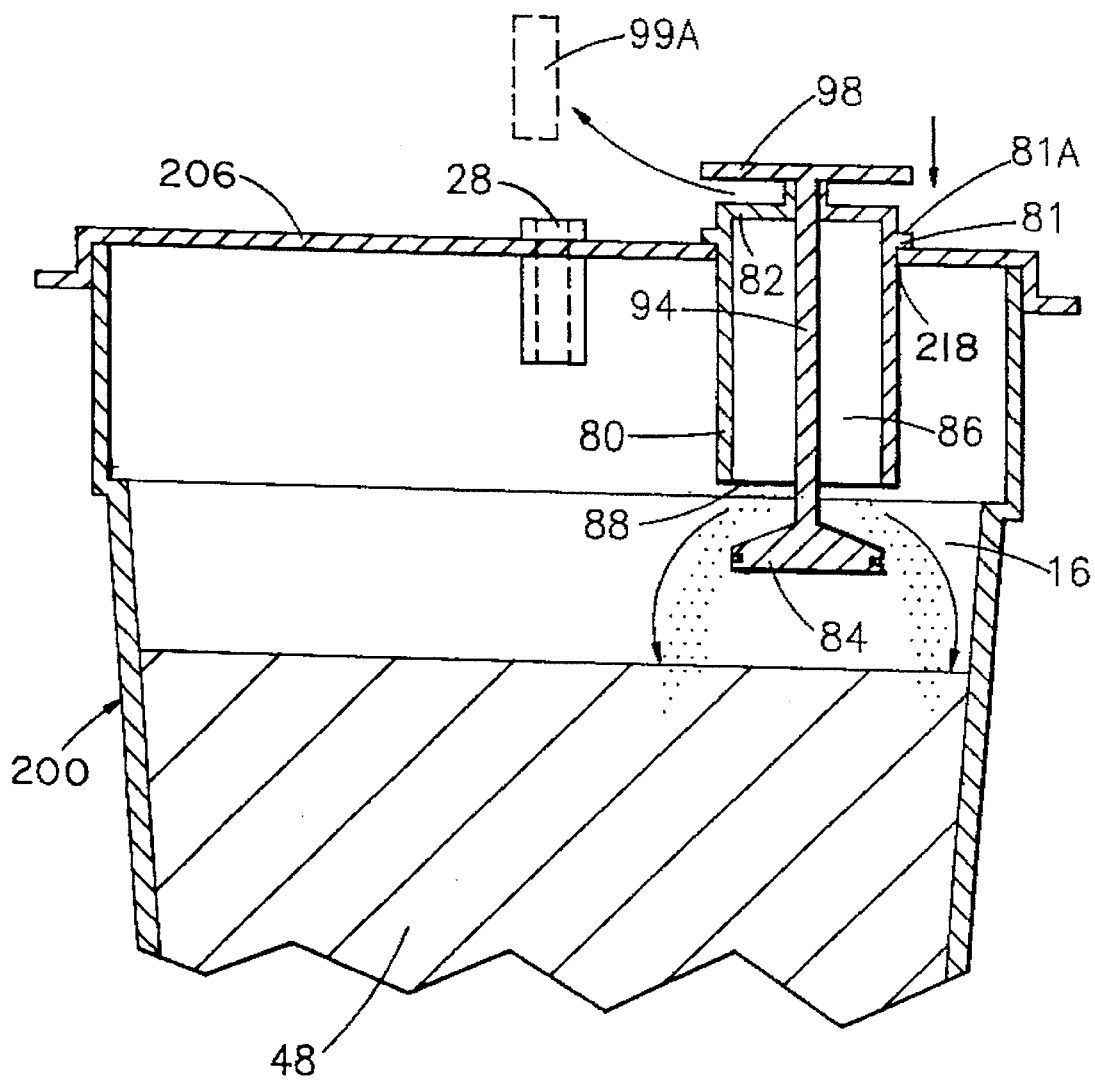
FIG. 23 is a sectional view showing a waste treatment material dispensing device located on a medical waste fluids disposal vessel lid having a plunger in an activated position.

As illustrated in FIGS. 21, 22 and 23, canister 200 has a canister lid 206 containing body waste fluids 12 in storage volume 16 and covered by a canister lid 206 having an inlet port 26, a vacuum port 28, and an aperture 218. An independent container 78 has a cylindrical wall 80, and opposed upper and lower walls 82 and 84, respectively, that together define sealed chamber 86. Sealed chamber 86 holds xerogel composition 42, disinfectant 70 (not shown), or combination thereof, and is provided with a release device 90. Container 78 is sealably positioned in aperture 218 secured to lid 206 by sealing ring 81. Chamber 86 has an exit port 88 with lower wall 84 being removably mounted to cylindrical wall at exit port 88. A release device 90 mounted to container 78 includes lower wall 84 being a release head configured as a cone slidably mounted in chamber 86 and a vertical plunger rod 94 connected to the conical axis of lower release head 84 and slidably extending through upper wall 82 to a top end 95 (FIG. 21) spaced at a distance above upper wall 82. Conical lower wall release head 84 has an O-ring 96 mounted about its circumference so as to seal chamber 86. A plunger rod cap 98 at top end 95 of plunger rod 94 provides a surface for manual operation of plunger rod 94. A plastic peelable stop ring 99 is mounted around plunger rod 94 between upper wall 82 and cap 98; stop ring 99 prevents accidental movement of plunger rod 94. Prior to activation of plunger rod by pulling from a vertical slit (not shown) in stop ring 99 in a manner known in the art. Plunger rod 94 is for moving lower wall release head 84 between an inactive position (FIG. 21 and 22) and an activated position (FIG. 23), the inactive position being when lower wall release head 84 is located at exit port 88, and the activated position being when lower wall release head 84 is moved to a position below exit port 88, so that waste treatment material, e.g. xerogel composition 42, disinfectant 70, or combination thereof, is released from chamber 86 for downward movement into storage volume 16 of canister 200 for mixture therein with body waste fluids 12 resulting in the formation of a solidified mixture, or insoluble gel 48 (FIG. 23) in storage volume 16.

Figure 24:
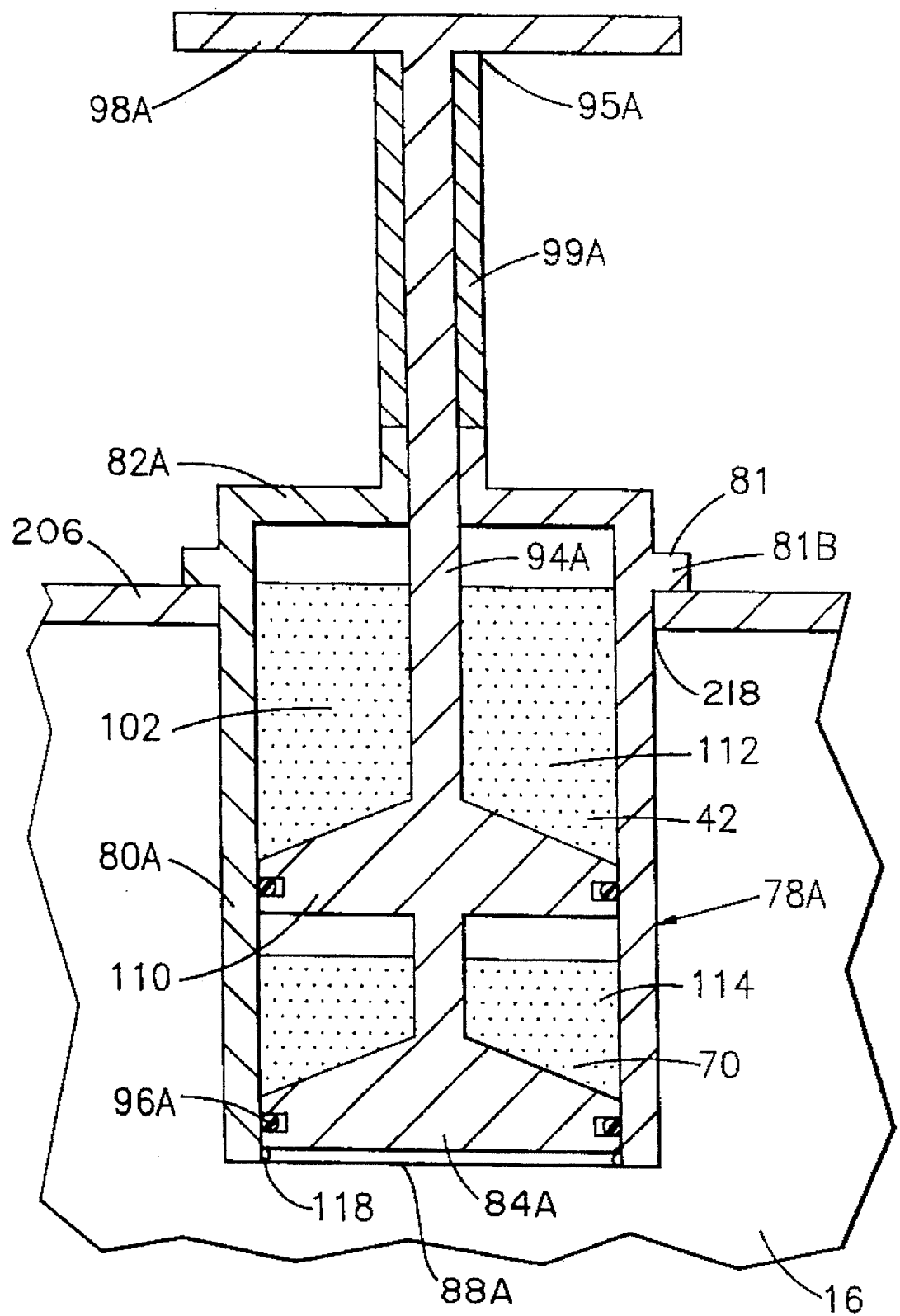
FIG. 24 is a fragmented sectional view showing a waste treatment material dispensing device having xerogel powder and a disinfectant and having a plunger in an inactive position.
Figure 25:
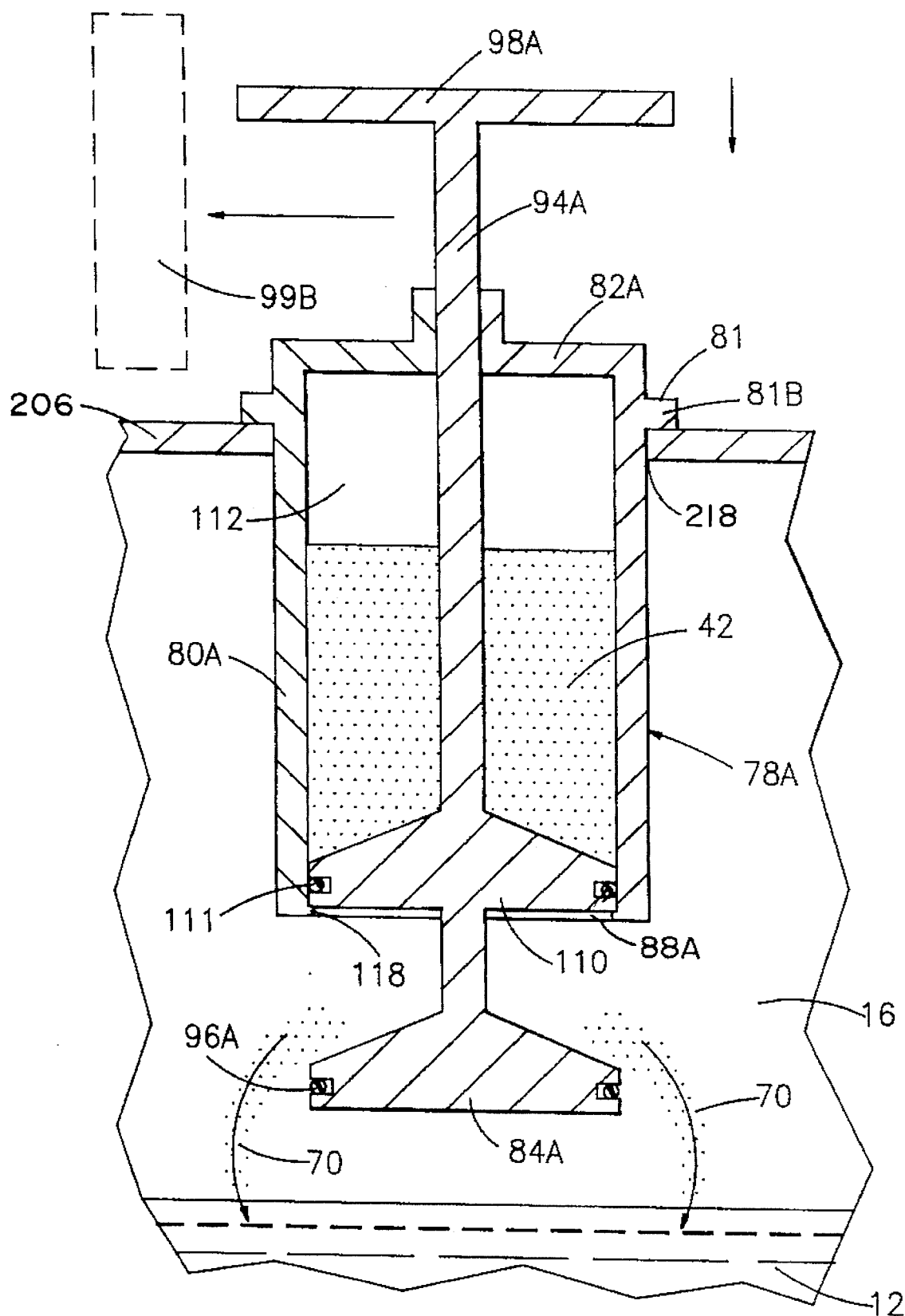
FIG. 25 is a fragmented sectional view showing a waste treatment material dispensing device having xerogel powder and a disinfectant and having a plunger in a semi-activated position.
Figure 26:
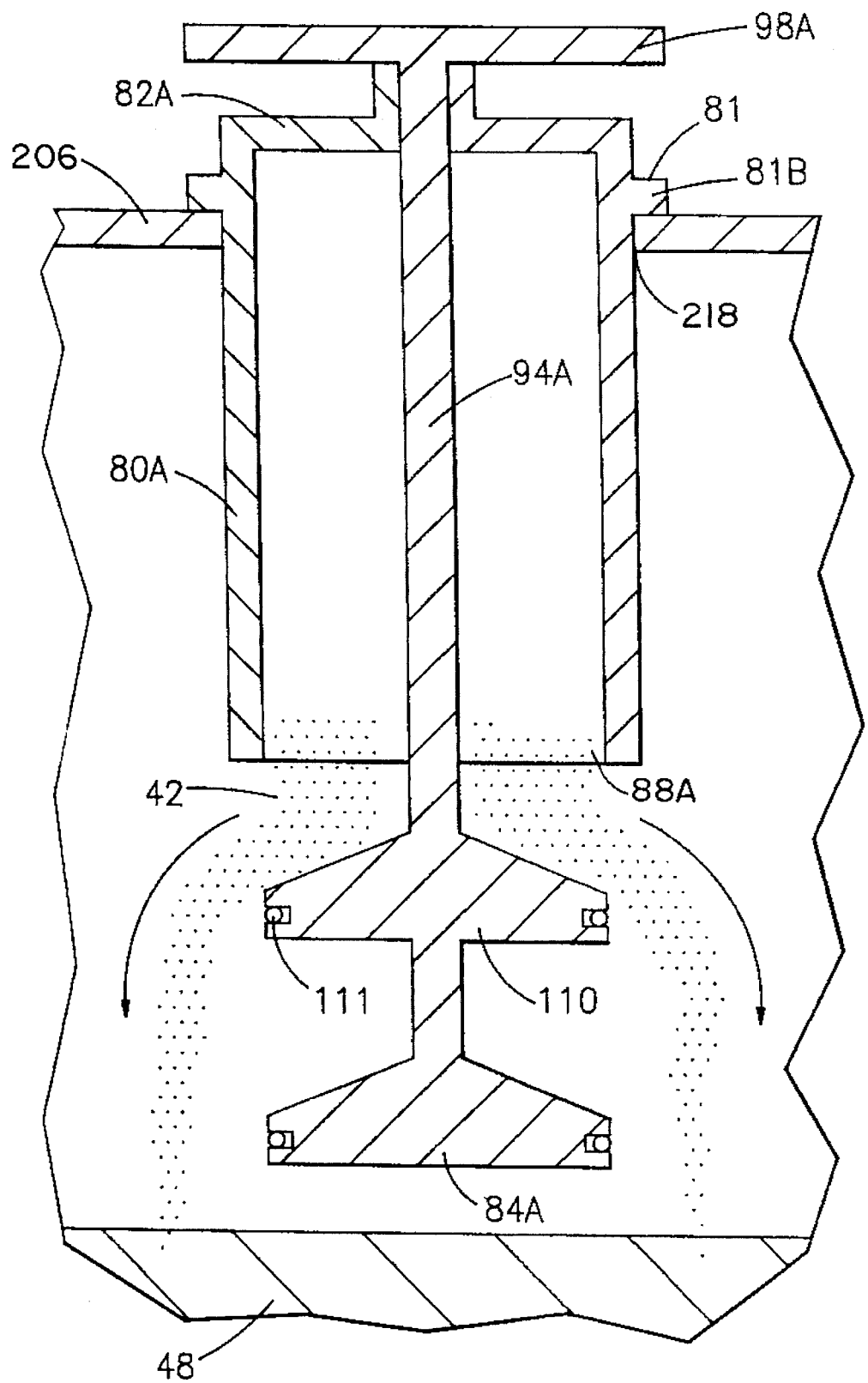
FIG. 26 is a fragmented sectional view showing a waste treatment material dispensing device having xerogel powder and a disinfectant and having a plunger in a fully-activated position.

FIGS. 24, 25, and 26 illustrate a canister lid 206 having aperture 218. A container 78A includes a continuous, cylindrical upright wall 80A configured as a cylinder, and an upper wall 82A and an opposed, cone-shaped lower wall, or release head, 84A that together define a sealed chamber 86A. Container 78A is sealably positioned in aperture 218. Chamber 86A has an exit port 88A (FIG. 26) with lower wall 84A being removably mounted to cylindrical wall 80A at exit port 88A. A release device 102 mounted to container 78A includes a release head 84A and a vertical plunger rod 94A connected to the conical axis of release head 84A and slidably extending through upper wall 82A to a top end 98A spaced above upper wall 82A. Conical release head 84A has an O-ring 96A mounted about its circumference as to seal chamber 86A. A plunger rod cap 98A at the top end of plunger rod 94A provides a surface for manual operation of plunger rod 94A.

As illustrated in FIG. 24, movable intermediate sealing wall 110 is in an inactive position, and is located within chamber 86A between and lateral to upper end lower chamber walls 82A and 84A forming from chamber 86A upper and lower compartments 112 and 114, respectively. Upper compartment 112 contains waste treatment material, e.g. xerogel powder composition 42, at least one disinfectant 70, or combination thereof, and lower compartment 114 contains waste treatment material, e.g. at least one disinfectant 70 in the form of a powder. Plunger rod 94A is connected with intermediate release head 110 at the axis of its cone. Plunger rod 94A is for moving release head 84A and intermediate release head 110 from an inactive position to a semiactivated position (FIG. 25) and then to an activated position (FIG. 26). The inactive position is when intermediate release head 84A is located at exit port 88A; the semiactivated position is when intermediate release head 84A is positioned below exit port 88A and intermediate release head 110 is positioned in alignment with exit port 88A wherein disinfectant 70 is released from lower compartment 114 for movement into storage volume 16 of canister 200 for mixture therein with body waste fluids 12 resulting in the destruction, or at least deactivation of body waste fluids 12 in storage volume 16, and intermediate release head 110 is positioned at exit port 88A; and the activated position is when release head 110 has been moved below exit port 88A wherein xerogel composition 42 is released from upper compartment 112 into storage volume 16 for mixture therein with the sterilized body waste fluids 12 resulting in the formation of a solidified mixture 48 (FIG. 26) in storage volume 16.

Removable interlocking strips 99 (FIG. 22) and 99A (FIG. 23) connected to plunger rods 94 and 94A, respectively, between upper walls 82 and 82A and caps 98 and 98A, respectively, maintain plunger rods 94 and 94A at the respective distances between upper walls 82 and 82A and upper walls 82 and 82A, respectively, until manually removed, e.g. strip 99B (FIG. 25) in preparation for activation of plunger rods 94 and 94A. Locking strip 116 is separated at a vertical line 118 and is preferably made of a thin resilient plastic.

Containers 32, 78, 78A, 102, 104, and 106 can be independent of lids 206 and mountable to lids 206 as shown and described analogous to containers 32 and 32A. In such independent systems a ring stop member 81B shown in FIGS. 24–26 is, optionally, integral with container walls 34 and 34A. Containers 78 or 78A are mountable into pre-existing drainage ports 30C shown in FIGS. 19–24 defined in lids 206 after removal of their drainage port caps (not shown). Container walls 80 and 80A can be tapered for press of friction fit into drainage ports 30C.

All connections between the containers, e.g. container 200, and the lids, e.g. lid 206 (FIGS. 13 and 14) can be threaded connections or by bayonet connections known in the art, neither of which connections are specifically shown.

Several types of waste treatment material and compositions are used in the present invention including disinfectants, xerogels, and combinations thereof. As used herein, the terms, "composition" and "waste treatment material" are used interchangeably. Compositions further comprise at least one disinfectant selected from the group comprising germicides such as bactericides, bacteriostats, fungicides and the like to render infectious components of said fluids non-infectious.

Disinfectants which may be used in preparing a composition of the invention are known to the art and include chlorine releasing compounds, such as Lysol™ powdered bleach; iodine releasing compositions, e.g., iodophors as such as Povidone™-iodine; oxidants, such as benzoyl peroxide, alcohols such as ethanol, carbonyl compounds such as acetone and ionic and nonionic detergents including soaps, Non-idet™, and Triton™X -100 and quaternary ammonium compounds and the like and mixtures thereof. In that respect xerogels comprising pendant ionic groups such as quaternary ammonium and phosphonato or sulfonato are both hydrophilic and disinfecting without the addition of other disinfecting components. The compositions of the invention may be added to the waste fluids in the form of free-flowing powders, compacted tablets, and the like.

Disinfectant 70 (FIGS. 6, 15, 20, 24, and 25) comprises at least one disinfectant to destroy infectious substances within body waste fluids 12 upon interaction therewith. A composition including disinfectant 70, by way of example, is selected from the group comprising quaternary ammonium compounds, alcohols, phenols, aldehydes and ketones, chlorine releasing agents, iodine releasing agents, nonionic, cationic and anionic detergents, oxidants, phenols, phenolic aldehydes, hexachlorophene chlorhexidine gluconate, precursors for the above, and the like, and salts and mixtures thereof.

Disinfectant 70 is also selected from the group comprising germicides such as bactericides, bacteriostats, fungicides, and the like, to destroy and, if desired, disinfect infectious components of body waste fluids 12.

Waste treatment material and compositions of the present invention include xerogels. Xerogel composition 42 specified in each of the several embodiments set forth above comprises at least one water-insoluble hydrophilic polymer. Xerogel composition 42 is selected from the group comprising partially hydrolyzed poly(vinyl acetate), cross-linked poly (vinyl alcohol), cross-linked hydroxyalkyl acrylates and methacrylates, polymers and copolymers of ethylene oxide and polymers and copolymers acrylamide. Xerogel composition 42 is further selected from the group comprising acrylonitrile - acrylamide copolymers, poly(ethylene oxide) polymers and copolymers, cellulose - starch - acrylates and ground corn husks.

Xerogel composition 42 and disinfectant 70 may be premixed and the admixture subsequently added to body waste fluids 12 wherein the chambers for those systems are described as containing xerogel composition 42. However, when xerogel compositions and disinfectants are mixed together, the xerogel composition and disinfectant must be checked to determine whether or not their mixture will result in the degradation of one compound or the other.

As will be appreciated, this invention relates to the safe disposal of non-gaseous fluid waste materials. More, particularly it relates to a composition for use in the disposal of non-gaseous waste fluids such as blood, drained from body cavities of patients pre- and post- operatively as well as during operations. As described herein, the compositions comprise at least one hydrophilic water-insoluble polymer in several embodiments referred to herein. If desired, said composition further comprises materials for disinfecting said fluids.

Preferably the compositions will be present in collection container 200 (FIGS. 1, 6, 10, 13, 14, 18–23), from the beginning of the collection procedure, but separated from the fluids 12 by a frangible separation interposed therebetween until mixing of fluids 12 and the inventive compositions, e.g. waste treatment material 144, is required. The composition may be contained in a compartment, e.g. device 102 (FIGS. 1 and 2), device 104 (FIGS. 6 and 8), device 106 (FIGS. 9 and 10), container 32 (FIGS. 15–17), container 32A (FIGS. 18 and 19), container 32B (FIG. 20), container 78 (FIGS. 21–23), container 78A (FIG. 24–26), within a container, e.g. canister 200, flexible walled collection vessel 204, or a combination thereof (FIGS. 13–14), and separated from the collecting compartment, e.g. canister 200 or flexible walled collection vessel 204, or combination thereof by a frangible wall, e.g. walls 138, 300 wherein the walls of said compartment may be burst by methods known in the art, including a pointed rod entering said compartment from outside the container through a ring seal in the outside wall thereof. Other methods, by way of example, include the use of punch head 50 (FIGS. 15–20).

In that aspect, when mixing of the composition of the invention, e.g. waste treatment material 144, and the fluids 12 (FIGS. 1, 6, 15, 16, 18–22, and 25) is desired the rod is forced through the wall of the compartment permitting the inventive composition to be discharged therefrom into the collecting chamber, e.g. storage volume 16 (FIGS. 1, 6, 10, 15–25) and mixed with the waste fluids 12 to render them non-flowable (FIGS. 23 and 26) and disinfected.

It will also be appreciated that the invention also provides a method for preparing waste fluids 12 for safe disposal which comprises the steps of adding a composition comprising at least one xerogel comprising at least one water-insoluble hydrophilic polymer to said fluids and mixing same until essentially all of said fluids have been absorbed by said composition the resultant product being essentially non-flowable. The composition is present in the collection vessel, e.g. vessel 204, canister 200, or combination thereof, and separated from the fluids 12 therein, in a compartment, e.g. device 102 (FIGS. 1 and 2), device 104 (FIGS. 6 and 8), device 106 (FIGS. 9 and 10), container 32 (FIGS. 15–17), container 32A (FIGS. 18 and 19), container 32B (FIG. 20), container 78 (FIGS. 21–23), container 78A (FIG. 24–26), which may be opened, when desired, to permit mixing of the contents thereof with the waste fluids 12. The compartment comprises a chamber in the vessel comprising at least one frangible wall to separate the contents thereof from the contents of the vessel wherein said wall may be opened to permit mixing of the contents of the vessel and compartment.

Figure 27:
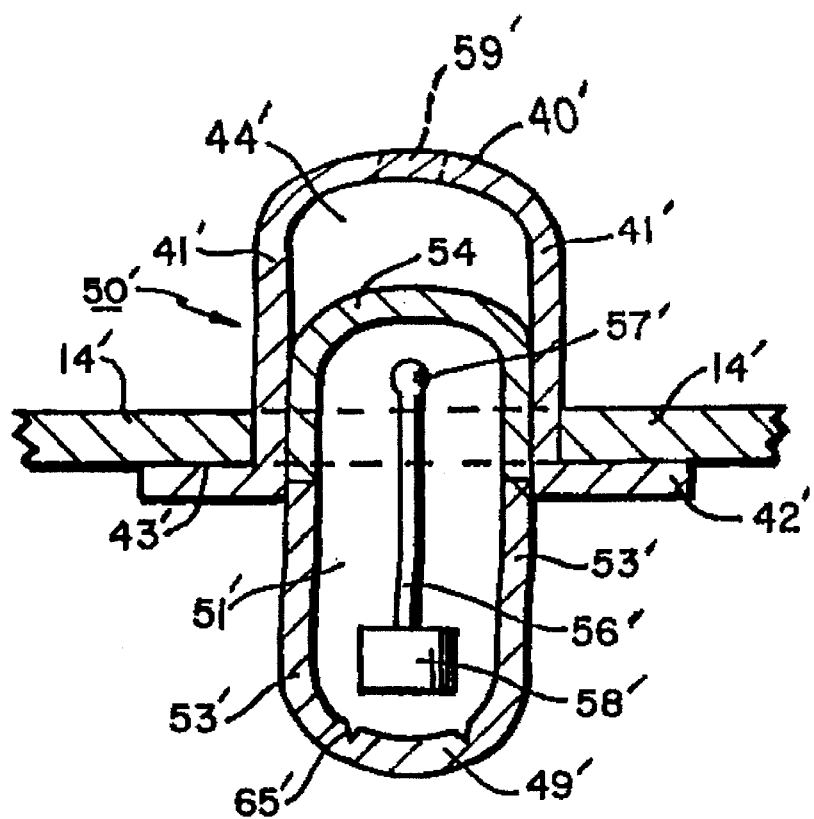
FIG. 27 is a sectional view showing a waste treatment material dispensing device having a plunger in an inactivated position.

As illustrated in FIG. 27 container 50' comprises a plunger means 51' for separating a bottom portion 52', by applying pressure thereto, from the side walls 53' of said container. The upper wall and an upper portion of the side walls indicated by numerals 54' and 55', respectively, of the container 50' comprise a flexible, distortable material through which pressure may be applied to the top 57' of the plunger means described below.

The plunger means, examples of which are well known in the art, comprises a thin elongated member 56' which can receive pressure applied thereto, through means 57' at its top, whereby it is caused to descend thereby causing approximately horizontal means 58' at its lower end to push out a portion of the lower wall 52' of container 50', thereby permitting the composition contained therein to mix and interact with the contents of the vessel.

In this embodiment, a section 59' of the upper wall 40' of housing 39' comprises a flexible material which may be depressed by slight pressure thereon to apply pressure to the plunger means causing it to descend.

If desired, the upper portion housing 39' may be covered by a removable cap (not shown) to prevent premature depression of said section 59'.

Figure 28:
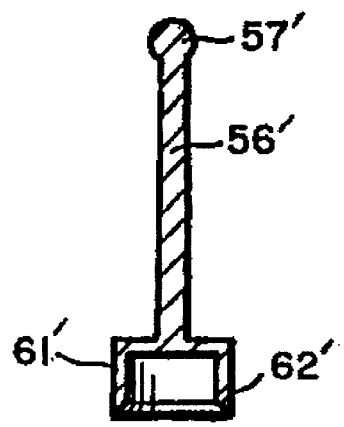
FIG. 28 is a sectional view of a plunger of FIG. 27.

FIG. 28 illustrates a modification of this embodiment in which the horizontal means 58' of the plunger is replaced by a hollow chamber, comprising a horizontal upper wall 60' sealed to the bottom of said trunk 45', and side walls 61' descending therefrom. The side walls terminate at beveled knife edges 62' which, when pressure is applied to the plunger through means 57', cut through the bottom wall 52' of the container 50' so as to cause a portion thereof to be separated from the container whereby its contents are released to the vessel to act as indicated above.

If desired, the bottom walls 49' of the containers 45' may be prescored as at 65' to facilitate the separation of the bottom walls of the container 45'.

Figure 29:
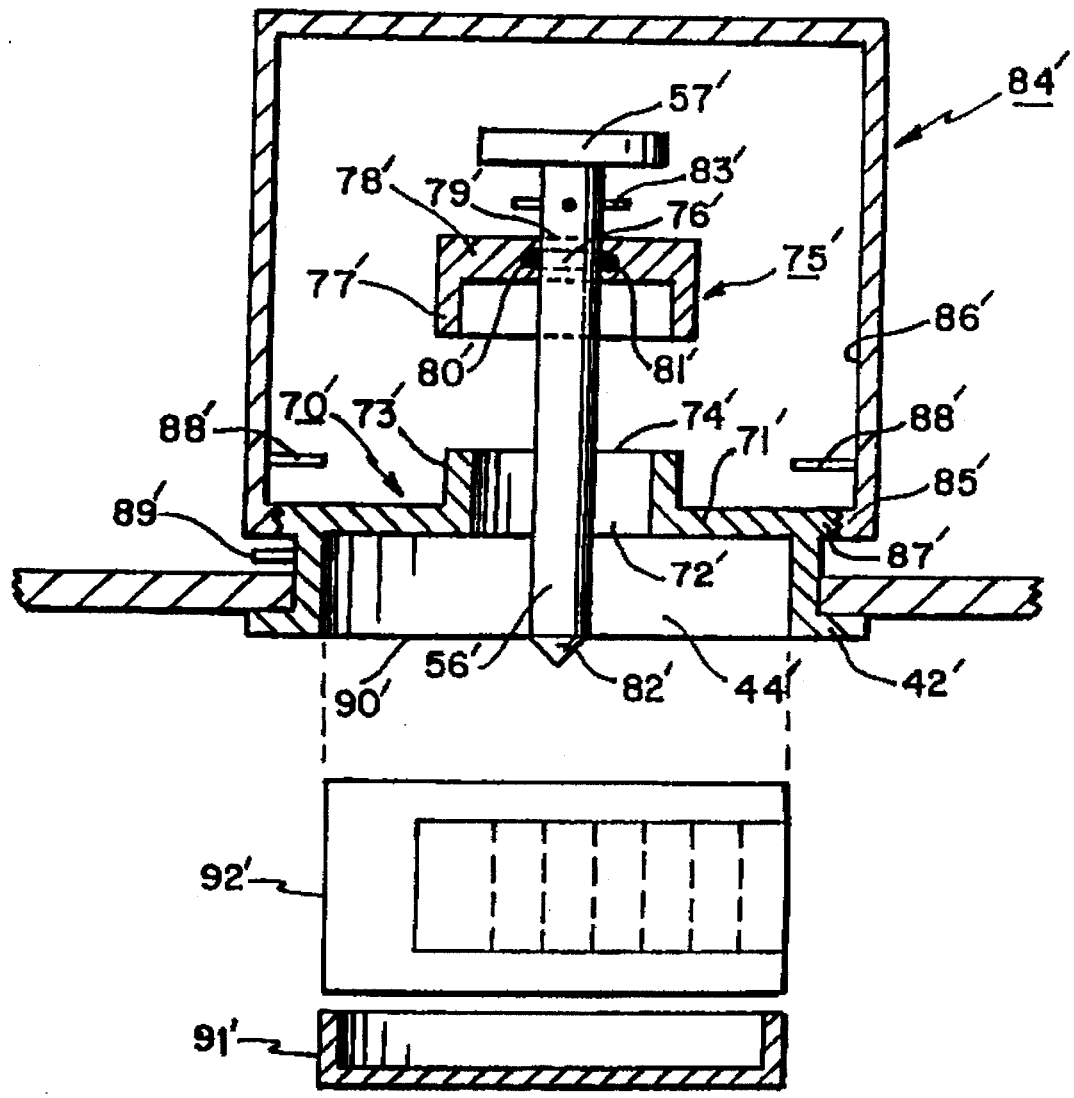
FIG. 29 is a sectional view showing a waste treatment material dispensing device having a plunger in an inactivated position.

FIG. 29 illustrates another embodiment a waste treatment material dispensing device comprising a housing 70', comprising an upper wall 71' situated above the plane of the cap 14', from which there descends side walls 41' terminating in a flange 42', extending normally outward therefrom and sealed to the underside of cap 14' at 43'. The housing encompasses a chamber 44' comprising a large bottom opening to receive a sealed container containing a composition according to the invention. The upper wall 71' comprises a small opening 72' through which the lower portion of the elongated member 56' of the plunger means can pass.

A ring 73', rises normally upward from the edges of said opening and terminates in opening 74'.

The opening 74' is encompassed by cap means 75' having a port 76' through which said member 56' can pass into the chamber 44'.

If desired, the cap means may comprise a flexible, e.g., rubber tube comprising a bottom wall comprising a large bottom opening through which the side walls of said ring 73' may pass. The inner portion of the side walls 77' of the cap being in contact with and surrounding the outer portion of the side walls 73' of the ring, and an upper wall 78' comprising a small upper port 79' has a diameter slightly less than that of the elongated member 56'.

In a modification of the above embodiment, the cap means may comprise a rigid cap, which may be attached to the housing 70' by known means, e.g., matching threaded portions on the inner portion of the side walls of said port comprising a circumferential groove 80' for receiving a flexible O-ring 81'.

The plunger means comprises an elongated member 56' comprising a flat, hemispherical or pointed portion 82'. At its upper end the plunger is terminated by handle means 57'. The elongated member of the plunger means is passed through opening 79' and port 76' into sealed contact with the walls of the opening of the above-indicated flexible tube 75' or the O-ring of the rigid cap 75'. The elongated member may further comprise a plurality of break-away tabs 83' which will prevent inadvertent depression, under an accidentally applied slight pressure, of the plunger, but will breakaway, under an intentionally applied greater pressure, to permit depression of the plunger into chamber 44'.

It will often be desirable to provide means to cover the addition means of the invention to prevent accidental depression of the plunger means.

Such cover means, as known to the art, include cap means 84' which comprises a threaded portion 85', on its inner wall, to engage complementary outer threads 87' on the side wall of housing 70'. Means are provided either on the cap 84', as at 88', projecting normally inwardly from the inner portion 86' of the side wall thereof, or on the housing 70', as at 89', projecting normally outwardly from the outer portion of the side wall 41' thereof, to prevent the cover from descending too low and depressing the plunger means.

In the use of this embodiment of the invention a sealed container 92', as described above, containing any of the above compositions of the invention is placed into chamber 44' the bottom opening 90' of which is sealed by an easily detachable cover 91'.

When it is desired to have the composition of the invention, contained in said container to mix with the waste fluids, the cap means 84' is removed, pressure is applied to the handle 57' of the plunger means thereby causing it to descend into chamber 44'.

Depending upon the position of said container 92' the plunger means will either press on the upper surface thereof causing it to descend and force the easily detachable cover 91' to separate from the flange 42', or the plunger means itself will force the cover 91' to detach, whereby the container will be caused to enter the chamber of the collection vessel to be contacted by the waste fluids and release its contents to mix with and immobilize and, if desired, disinfect said fluids.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

I claim:

1. A closed body waste fluids collection container for use in the disposal of waste fluids drained from a body cavity of a patient, said container having inlet and outlet ports disposed thereon, comprising:

(a) a collecting compartment for collecting body waste fluids drained from a patient;

(b) a composition disposed on said container, said composition for treating body waste fluids;

(c) a frangible separation interposed between said composition and said collecting compartment, said frangible separation retaining said composition; and, (d) an actuator for penetrating said frangible separation, said composition discharging into said collecting compartment upon actuation of said actuator.

2. The body waste fluids collection container of claim 1 wherein said actuator comprises a rod for penetrating said frangible separation.

3. The body waste fluids collection container of claim 1 wherein said collecting compartment comprises a flexible walled collection vessel.

4. The body waste fluids collection container of claim 1 wherein said collecting compartment further comprises a flexible walled collection vessel, said flexible walled collection vessel disposed within a rigid walled canister.

5. The body waste fluids collection container of claim 1 wherein said collecting compartment further comprises a flexible walled collection vessel, said flexible walled collection vessel disposed within a rigid walled canister, and said flexible walled collection vessel comprising an integral lid.

6. The body waste fluids collection container of claim 1 wherein said collecting compartment further comprises a flexible walled collection vessel, said flexible walled collection vessel disposed within a rigid walled canister, said flexible walled collection vessel comprising a lid, said lid having an inlet port for connecting said collection container to a patient, and said lid having a vacuum port for connecting said collection container to a vacuum machine.

7. The body waste fluids collection container of claim 1 wherein said composition comprises at least one disinfectant.

8. A body waste fluids collecting container for use in the disposal of waste fluids drained from a body cavity of a patient, said container having inlet and outlet ports, comprising:

(a) a collecting compartment for collecting body waste fluids drained from a patient;

(b) a retaining compartment disposed within said container;

(c) a composition for treating body waste fluids, said composition disposed within said retaining compartment;

(d) at least one wall disposed on said retaining compartment, said wall separating said composition from said collecting compartment; and, (e) an actuator for opening said wall, said actuator permitting release of said composition from said retaining compartment upon actuation.

\* \* \* \* \*